(12) United States Patent
Chadeayne

(10) Patent No.: US 12,017,991 B2
(45) Date of Patent: Jun. 25, 2024

(54) QUATERNARY TRYPTAMINES AND THEIR THERAPEUTIC USES

(71) Applicant: CAAMTECH, INC., Issaquah, WA (US)

(72) Inventor: Andrew R Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

(21) Appl. No.: 18/260,853

(22) PCT Filed: Jan. 10, 2022

(86) PCT No.: PCT/US2022/011755
§ 371 (c)(1),
(2) Date: Jul. 10, 2023

(87) PCT Pub. No.: WO2022/150675
PCT Pub. Date: Jul. 14, 2022

(65) Prior Publication Data
US 2023/0416200 A1 Dec. 28, 2023

Related U.S. Application Data

(60) Provisional application No. 63/188,745, filed on May 14, 2021, provisional application No. 63/135,910, filed on Jan. 11, 2021.

(51) Int. Cl.
*C07D 209/16* (2006.01)
*A61K 31/4045* (2006.01)
(Continued)

(52) U.S. Cl.
CPC ........ *C07D 209/16* (2013.01); *A61K 31/4045* (2013.01); *A61K 38/44* (2013.01); *A61K 45/06* (2013.01); *C12P 17/165* (2013.01)

(58) Field of Classification Search
CPC .................................................. C07D 209/16
See application file for complete search history.

(56) References Cited

U.S. PATENT DOCUMENTS 3,078,214 A 2/1963 Hofmann et al.
6,306,181 B1 10/2001 Terranova
(Continued)

FOREIGN PATENT DOCUMENTS

WO 9500478 A1 1/1995

OTHER PUBLICATIONS

International Search Report and Written Opinion of PCT International Application No. PCT/US2022/011755, dated May 11, 2022.

"Pubchem CID 45042573" Create Date: Mar. 29, 2010 (Mar. 29, 2010) Date Accessed: Apr. 22, 2022 (Apr. 22, 2022); p. 2.
Bradley et al., (1970). "Origin and Mechanism of Hallucinations," edited byW. Keup, pp. 333-344. New York: Plenum Press.
Cameron et al., (2018) "Dark Classics in Chemical Neuroscience: N,N-Dimethyltriptamine (DMT)," Chem. Neurosci. 9, 2344-2357.
Carhart-Harris et al., (2017) "The Therapeutic Potential of Psychedelic Drugs: Past, Present, and Future," Neuropsychopharmacology, 42, 2105-2113.

(Continued)

*Primary Examiner* — Yong S. Chong
(74) *Attorney, Agent, or Firm* — RAPHAEL BELLUM PLLC

(57) ABSTRACT

The disclosure relates to compounds of formula (I): Among the substituents in a compound of formula (I), one of $R_4$ and $R_5$ is hydrogen and the other of $R_4$ and $R_5$ is —$OSC_2Rs_6$. The disclosure relates to compounds of formula (II): Among the substituents in a compound of formula (II), $R_6$ is a halogen chosen from F, Cl, Br, and I. The disclosure relates to compositions comprising a compound of formulas (I) or (II) and an excipient. The disclosure relates to pharmaceutical compositions comprising a therapeutically effective amount of a compound of formulas (I) or (II). The disclosure relates to therapeutic uses of compounds of formulas (I) or (II). The disclosure relates to compounds of formula (II), including 5-fluoro-N,N,N-trimethyltryptammonium iodide, 5-fluoro-N,N,N-triethyltryptammonium iodide, 5-fluoro-N,N,N-tri-n-propyltryptammonium iodide, 5-chloro-N,N,N-trimethyltrptammonium iodide, 5-chloro-N,N,N-triethyl-tryptammonium iodide, 5-bromo-N,N,N-triethyltryptammonium iodide, 5-bromo-N,N,N-tri-n-propyltryptammonium iodide, and 5-bromo-N,N,N-tri-n-propyltryptammonium iodide acetonitrile solvate and their crystalline forms and their compositions and uses.

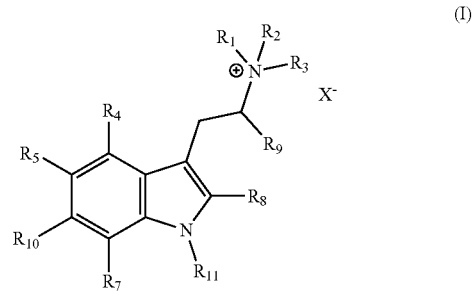

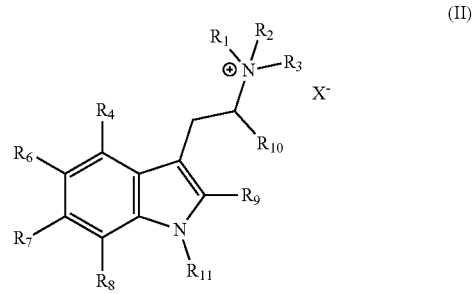

15 Claims, 16 Drawing Sheets

(51) Int. Cl.
*A61K 38/44* (2006.01)
*A61K 45/06* (2006.01)
*C12P 17/16* (2006.01)

(56) References Cited

U.S. PATENT DOCUMENTS

2018/0221396 A1 8/2018 Chadeayne
2019/0142851 A1 5/2019 Chadeayne
2019/0192498 A1 6/2019 Stamets
2020/0331939 A1 10/2020 Londesbrough

OTHER PUBLICATIONS

Dinis-Oliveira et al., (2017) "Metabolism of Psilocybin and Psilocin: Clinical and Forensic Toxicological Relevance," Drug Metab. Rev. 49, 84-91.
Johnson et al., (2017) "Potential Therapeutic Effects of Psilocybin," Neurotherapeutics, 14, 734-740.
McKenna et al., (1990) "Differential Interactions of Indolealkylamines With 5-Hydroxytryptamine Receptor Subtypes," Neuropharmacology, 29, 193-198.
Gartz, (1989) "Analysis of Aeruginascin in Fruit Bodies of the Mushroom Inocybe aeruginascens," Int. J. Crude Drug Res., 27, 141-144.
Jensen et al., (2006) "Aeruginascin, a Trimethylammonium Analogue of Psilocybin from the Hallucinogenic Mushroom Inocybe aeruginascens," Planta Med., 72, 665-666.
Nichols, (2012) "Structure-activity relationships of serotonin 5-HT2A agonists," WIREs Membr. Transp. Signal. 1, 559-579.
Repke et al., (1985) "Psychotomimetic N-Methyl-N-isopropyltryptamines. Effects of Variation of Aromatic Oxygen Substituents," Journal of Medicinal Chemistry 28(7), 892-896.
Sherwood et al., (2020) "Synthesis and Biological Evaluation of Tryptamines Found in Hallucinogenic Mushrooms: Norbaeocystin, Baeocystin, Norpsilocin, and Aeruginascin," J. Nat. Prod. 83, 461-467.
Chadeayne et al., (2020) "Active Metabolite of Aeruginascin (4-Hydroxy-N,N,N-trimethyltryptamine): Synthesis, Structure, and Serotonergic Binding Affinity," ACS Omega, 5, 27, 16940-16943.
Dolomanov et al., (2009) "OLEX2: A complete structure solution, refinement and analysis program," J. Appl. Cryst. 42, 339-341.
Sheldrick, (2015) "Crystal structure refinement with SHELXL," Acta Cryst., C71, 3-8.
Sheldrick, (2015) "SHELXT—Integrated space-group and crystal structure determination," Acta Cryst., A71, 3-8.
Milne et al., (2020) "Metabolic engineering of *Saccharomyces cerevisiae* for the de novo production of psilocybin and related tryptamine derivatives," Metabolic Engineering, 60, 25-36.
International Preliminary Report on Patentability for PCT International Application No. PCT/US2022/011755, dated Jul. 4, 2023.
Lee et al., (1936), "A Study of Twenty-Three Quaternary Ammonium Iodides," J. Pharmacol. Exp. Ther. 56, 466-472.
Revell, (2020), "What We Know (and Don't) About Magic Mushroom Paralysis," https://www.vice.com/en-in/article-y3zp35/magic-mushroom-paralysis-heres-what-we-know (Accessed Jul. 2020).
Weiland et al., (1934) "The constitution of bufotenine and bufotenidine. About toad toxins. VII," European Journal of Organic Chemistry, 513, 1-25.

QUATERNARY TRYPTAMINES AND THEIR THERAPEUTIC USES

CROSS-REFERENCE TO RELATED APPLICATIONS

This application claims priority to U.S. Provisional Application No. 63/135,910, filed on Jan. 11, 2021, and to U.S. Provisional Application No. 63/188,745, filed on May 14, 2021, the disclosures of which are incorporated by reference.

TECHNICAL FIELD

This disclosure relates to quaternary tryptamines, compositions, and pharmaceutical compositions containing them as well as their use in treating various diseases. In particular, this disclosure relates to quaternary amines and 5-halo quaternary tryptamines. The disclosure also relates to 5-halo quaternary tryptamines according to the disclosure including, 5-fluoro-N,N,N-trimethyltryptammonium iodide (5-F-TMT iodide), 5-fluoro-N,N,N-triethyltryptammonium iodide (5-F-TET iodide), 5-fluoro-N,N,N-tri-n-propyltryptammonium iodide (5-F-TPT iodide), 5-chloro-N,N,N-trimethyltrptammonium iodide (5-Cl-TMT iodide), 5-chloro-N,N,N-triethyltryptammonium iodide (5-Cl-TET iodide), 5-bromo-N,N,N-triethyltryptammonium iodide (5-Br-TET iodide), 5-bromo-N,N,N-tri-n-propyltryptammonium iodide (5-Br-TPT iodide), and 5-bromo-N,N,N-tri-n-propyltryptammonium iodide acetonitrile solvate (5-Br-TPT iodide acetonitrile solvate) and their crystalline forms.

BACKGROUND

N,N-dimethyltryptamine (DMT) and its derivatives have been used by humans for centuries because of their psychoactive, entheogenic, or hallucinogenic effects, or combinations thereof (Cameron & Olson, 2018). Psilocybin, the 4-phosphate variant of DMT, is arguably its most studied derivative. Psilocybin is one of several naturally occurring psychoactive tryptamines found in "magic" mushrooms. When consumed by humans, psilocybin serves as a prodrug of psilocin. Upon digestion, psilocybin hydrolyses to generate psilocin, the 4-hydroxy derivative of DMT. Psilocin is a potent serotonin 2a-agonist, which is responsible for its psychoactive properties (Dinis-Oliveira, 2017; Nichols, 2012).

Psychoactive tryptamines like DMT and psilocin have garnered significant interest recently because of their potential for treating mood disorders, including depression, anxiety, addiction, and post-traumatic stress disorder (PTSD) (Johnson & Griffiths, 2017; Carhart-Harris & Goodwin, 2017). Altering the chemical structure within this class of compounds can dramatically influence the potency and action of the drugs. For example, merely changing the N,N-dialkyl groups on DMT can modify its psychoactive properties: increasing the chain length of the two alkyl groups of the tryptamine to larger than n-butyl dramatically reduces or eliminates the psychoactive effects (Bradley & Johnston, 1970).

The synthesis of N-methyl-N-isopropyltryptamine (MiPT) was reported in 1981 (Repke et al., 1981). In 1985, Repke and co-workers reported that of the compounds in the series of N,N-dialkyl-4-hydroxytryptamines, the N-methyl-N-isopropyl derivative (4-HO-MiPT) is the most potent based upon qualitative effects on humans (Repke et al., 1985). Later quantitative studies showed the N-methyl-N-isopropyl derivatives of DMT and psilocin to be more potent as serotonin-1A, -2A and -2B receptors compared to the analogous dimethyl compounds (McKenna et al., 1990).

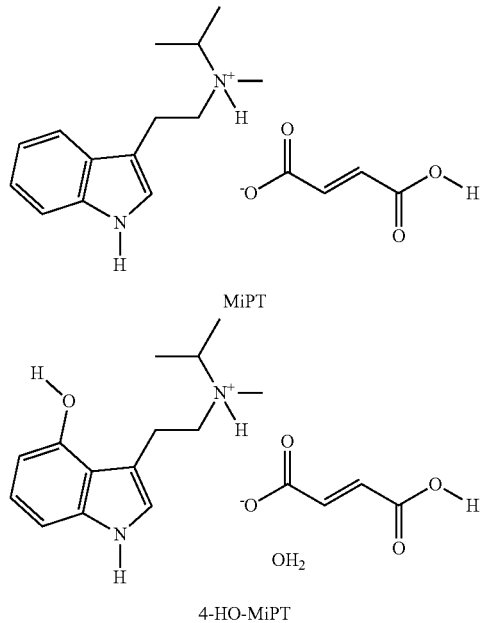

New psychoactive tryptamines have been identified in "magic mushrooms" as recently as 2017. (Lentz, et al., 2017.) Until this year, there was no general synthetic method for producing useful amounts of the minor psychoactive tryptamines. (Sherwood, Halberstadt, et al.) One of these minor components is aeruginascin, (Jensen, et al., 2006) the N-trimethyl analogue of psilocybin. The limited exposure of humans to *Inocybe aeruginascens* mushrooms, the only known species in which aeruginascin has been found, has resulted in hallucinations that exhibited only euphoric experiences. (Gartz, 1989). This is in contrast to psilocybin and psilocin mushrooms, which often lead to dysphoric moods during the psychedelic experience. Despite these observations, the pharmacological activity of aeruginascin has remained unexplored.

Substituted quaternary tryptammonium salts have been observed in nature going back to 1934 when bufotenidine, the N,N,N-tri-methyl analogue of serotonin, was observed in the excretions of toads (Wieland, et al. 1934). The unsubstituted N,N,N-tri-methyl-tryptammonium iodide was studied in 1936 and demonstrated nicotinic-stimulating action (Lee, et al. 1936). In 1987, Gartz first identified a quaternary tryptammonium in "magic mushrooms," which he called aeruginascin, N,N,N-tri-methyl-4-phosphoryloxytryptamine (Gartz, 1987). The tryptamines of "magic mushrooms" have garnered a great deal of interest of late as their psychotropic activity is being explored for the treatment of mental disorders including depression and anxiety (Johnson & Griffiths, 2017). Aeruginascin, in particular, has been featured in popular media for its potential to modulate the activity of psilocybin through an entourage effect (Farah, 2018), as well as its possible involvement in wood-lovers paralysis (Revell, 2020). The recent synthesis of aeruginascin (Sherwood, et al. 2020) and its active metabolite, 4-hydroxy-N,N,N-tri-methyl-tryptmine (Chadeayne, Pham, Reid, et al. 2020), as well as the biosynthetic production of both (Milne, et al. 2020) further demonstrate the attention that these molecules have received.

Although therapeutic efficacy is the primary concern for an active pharmaceutical ingredient (API), the salt and solid-state form (i.e., the crystalline or amorphous form) of a drug candidate can be critical to its pharmacological properties, such as bioavailability, and to its development as a viable API. Recently, crystalline forms of API's have been used to alter the physicochemical properties of an API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid-state properties of the crystalline form of the API, they can significantly impact the selection of a compound as an API, the ultimate pharmaceutical dosage form, the optimization of manufacturing processes, and absorption in the body. Moreover, finding the most adequate solid-state form for further drug development can reduce the time and the cost of that development.

Obtaining crystalline forms of an API is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process.

Even with the previous work, there is a need to develop new psilocybin derivatives with improved properties for treatment of psychological disorders.

SUMMARY

The disclosure relates to a quaternary amine compound of formula (I):

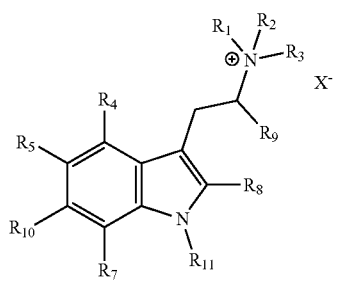

wherein:
$R_1$, $R_2$, and $R_3$ are each independently chosen from a $C_1$-$C_6$ alkyl or $C_2$-$C_6$ alkenyl;
one of $R_4$ and $R_5$ is hydrogen and the other of $R_4$ and $R_5$ is —$OSO_2R_6$;
$R_6$ is a $C_1$-$C_6$ alkyl or a substituted or unsubstituted aryl;
$R_7$, $R_8$, and $R_9$ are each independently hydrogen or $C_1$-$C_6$ alkyl;
$R_{10}$ is selected from hydrogen, $C_1$-$C_6$ alkyl, $C_2$-$C_6$ alkenyl, halogen, hydroxy, —$OR_6$, —$OC(O)R_6$, —$OC(O)OR_6$, or —$OSO_2R_6$;
$R_{11}$ is selected from hydrogen, $C_1$-$C_6$ alkyl, $C_2$-$C_6$ alkenyl, —$C(O)R_6$, —$C(O)OR_6$, or —$SO_2R_6$; and
$X^-$ is a pharmaceutically acceptable anion.

The disclosure also provides a method of making compounds of formula (I).

The disclosure further relates to a compound of formula (II):

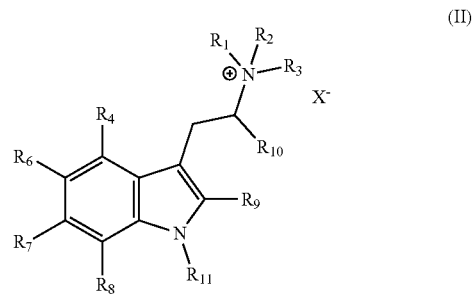

wherein:
$R_1$, $R_2$, and $R_3$ are each independently a straight chain or branched $C_1$-$C_6$ alkyl or $C_2$-$C_6$ alkenyl;
$R_4$ is hydrogen, hydroxy, —$OR_5$, —$OC(O)R_5$, —$OC(O)OR_5$, or —$OSO_2R_5$;
$R_5$ is a straight chain or branched $C_1$-$C_6$ alkyl or a substituted or unsubstituted aryl;
$R_6$ is a halogen chosen from F, Cl, Br, and I; and
$R_7$, $R_8$, $R_9$, and $R_{10}$ are each independently hydrogen or a straight chain or branched $C_1$-$C_6$ alkyl;
$R_{11}$ is selected from hydrogen, $C_1$-$C_6$ alkyl, $C_2$-$C_6$ alkenyl, —$C(O)R_5$, —$C(O)OR_5$, or —$SO_2R_5$; and
$X^-$ is a pharmaceutically acceptable anion.

In one embodiment, the disclosure relates to a compound of formula (II), with the proviso that when $R_1$, $R_2$, and $R_3$ are methyl and $R_4$, $R_7$, $R_8$, $R_9$, $R_{10}$, and $R_{11}$ are hydrogen, $R_6$ is not Br.

In one embodiment, the compound of formula (II) is a compound chosen from 5-fluoro-N,N,N-trimethyltryptammonium iodide (5-F-TMT iodide), 5-fluoro-N,N,N-triethyltryptammonium iodide (5-F-TET iodide), 5-fluoro-N,N,N-tri-n-propyltryptammonium iodide (5-F-TPT iodide), 5-chloro-N,N,N-trimethyltrptammonium iodide (5-Cl-TMT iodide), 5-chloro-N,N,N-triethyltryptammonium iodide (5-Cl-TET iodide), 5-bromo-N,N,N-triethyltryptammonium iodide (5-Br-TET iodide), 5-bromo-N,N,N-tri-n-propyltryptammonium iodide (5-Br-TPT iodide), and 5-bromo-N,N,N-tri-n-propyltryptammonium iodide acetonitrile solvate (5-Br-TPT iodide acetonitrile solvate). In embodiments, the aforementioned compounds are crystalline.

In one embodiment, the compound of formula (II) is crystalline 5-bromo-N,N,N-trimethyltryptammonium iodide (5-Br-TMT iodide).

The disclosure relates to compositions comprising a compound of formula (I) or formula (II), and an excipient. In one embodiment the excipient is a pharmaceutically acceptable excipient. The disclosure also relates to pharmaceutical compositions comprising a therapeutically effective amount of a compound of formula (I) or formula (II) and an excipient, wherein the excipient is a pharmaceutically acceptable carrier. The disclosure further relates to a method of preventing or treating a psychological disorder comprising the step of administering to a subject in need thereof a therapeutically effective amount of a compound of formula (I) or formula (II), or of a pharmaceutical composition containing one or more compounds of formula (I) or formula (II).

The disclosure also relates to a composition comprising as a first active component, the composition comprising: at least one compound of formula (I) or formula (II); at least one second active component selected from (a) a serotonergic drug, (b) a purified psilocybin derivative, (c) a purified cannabinoids, (d) a purified terpene, (e) an adrenergic drug, (f) a dopaminergic drug, (g) a monoamine oxidase inhibitor, (h) a purified erinacine, and (i) a purified hericenone; and a pharmaceutically acceptable excipient.

The disclosure further relates to methods of preventing or treating a physical and/or psychological disorders comprising the step of administering to a subject in need thereof an effective amount of a compound of formula (I) or formula (II), or a composition (e.g., a pharmaceutically-acceptable composition) comprising a compound of formula (I) or formula (II).

The disclosure also relates to methods of preventing or treating inflammation and/or pain comprising the step of administering to a subject in need thereof a therapeutically effective amount of a compound of formula (I) or formula (II), and to administering a composition (e.g., a pharmaceutically-acceptable composition) comprising a compound of formula (I) or formula (II).

The disclosure also relates to methods of preventing or treating inflammation and/or pain, preventing or treating a neurological disorder, modulating activity of a mitogen activating protein (MAP), modulating neurogenesis, or modulating neurite outgrowth comprising the step of administering to a subject in need thereof a therapeutically effective amount of a compound of formula (I) or formula (II), and to administering a pharmaceutical composition or a composition according to the disclosure.

The disclosure also relates to methods of preventing or treating sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

The disclosure also relates to methods of preventing or treating women's health disorders including, but not limited to, menstrual cramping, dysmenorrhea, post-hysterectomic pain, vaginal or vulvar vestibule mucosa disorder, vaginal atrophy, or vulvar vestibulitis.

The disclosure also relates to a method of generating a dialkyltryptamine compound in situ in a patient, the method comprising administering at least one quaternary tryptamine compound selected from formula (I) or (II) to the patient. The disclosure also relates to methods of generating a dialkyltryptamine compound comprising contacting at least one quaternary tryptamine compound selected from formula (I) or (II) with an enzyme in vitro or in vivo, such as an enzyme capable of nitrogen dealkylation (e.g., cytochrome P450 enzymes (CYPs)). The disclosure further relates to methods of generating a dialkyltryptamine compound in situ in a patient comprising contacting at least one quaternary tryptamine compound selected from formula (I) or (II) with an enzyme in the patient capable of nitrogen dealkylation (e.g., cytochrome P450 enzymes (CYPs)).

In one embodiment, crystalline 5-F-TMT iodide according to the disclosure is characterized by an orthorhombic, $P2_12_12_1$ crystal system space group at a temperature of about 297 K; unit cell dimensions a=7.7261 (4) Å, b=13.6571 (6) Å, and c=13.9972 (7) Å, or an XRPD having peaks at 13.1, 20.5, and 22.2° 2θ±0.2° 2θ.

In one embodiment, crystalline 5-F-TET iodide according to the disclosure is characterized by an orthorhombic, $P2_12_12_1$ crystal system space group at a temperature of about 297 K; unit cell dimensions a=8.5885 (4) Å, b=13.6650 (6) Å, and c=14.6306 (7) Å, or an XRPD having peaks at 13.6, 15.9, and 16.6° 2θ±0.2° 2θ.

In one embodiment, crystalline 5-F-TPT iodide according to the disclosure is characterized by a monoclinic, $P2_1/c$ crystal system space group at a temperature of about 297 K; unit cell dimensions a=17.8375 (9) Å, b=7.4586 (3) Å, c=16.4361 (7) Å, and β=110.228 (2°), or an XRPD having peaks at 10.6, 13.4, and 18.1° 2θ±0.2° 2θ.

In one embodiment, crystalline 5-Cl-TMT iodide according to the disclosure is characterized by a monoclinic, I2/a crystal system space group at a temperature of about 297 K; unit cell dimensions a=13.5105 (15) Å, b=14.1488 (8) Å, c=15.9096 (9) Å, and β=90.3840 (13°), or an XRPD having peaks at 11.1, 14.4, and 20.7° 2θ±0.2° 2θ.

In one embodiment, crystalline 5-Cl-TET iodide according to the disclosure is characterized by a triclinic, P¯1 crystal system space group at a temperature of about 297 K; unit cell dimensions a=12.4760 (13) Å, b=12.5317 (12) Å, c=13.9873 (16) Å, α=75.340 (3°), β=68.793 (4°), and γ=64.486 (3°), or an XRPD having peaks at 8.2, 9.1, and 12.1° 2θ±0.2° 2θ.

In one embodiment, crystalline 5-Br-TET iodide according to the disclosure is characterized by an orthorhombic, $P2_12_12_1$ crystal system space group at a temperature of about 297 K; unit cell dimensions a=9.5921 (4) Å, b=13.2918 (7) Å, and c=14.4411 (7) Å, or an XRPD having peaks at 11.1, 12.9, and 20.4° 2θ±0.2° 2θ.

In one embodiment, crystalline 5-Br-TPT iodide according to the disclosure is characterized by a monoclinic, $P2_1/c$ crystal system space group at a temperature of about 297 K; unit cell dimensions a=18.2646 (18) Å, b=7.6845 (8) Å, c=16.2828 (13) Å, and β=110.918 (3°), or an XRPD having peaks at 5.2, 10.4, and 13.1° 2θ±0.2° 2θ.

In one embodiment, crystalline 5-Br-TPT iodide acetonitrile solvate according to the disclosure is characterized by a monoclinic, $P2_1/c$ crystal system space group at a temperature of about 297 K; unit cell dimensions a=11.4346 (5) Å, b=14.8646 (5) Å, c=14.9080 (6) Å, and β=107.269 (1°), or an XRPD having peaks at 8.1, 10.0, and 11.9° 2θ±0.2° 2θ.

DETAILED DESCRIPTION

Compounds

Figure 1:
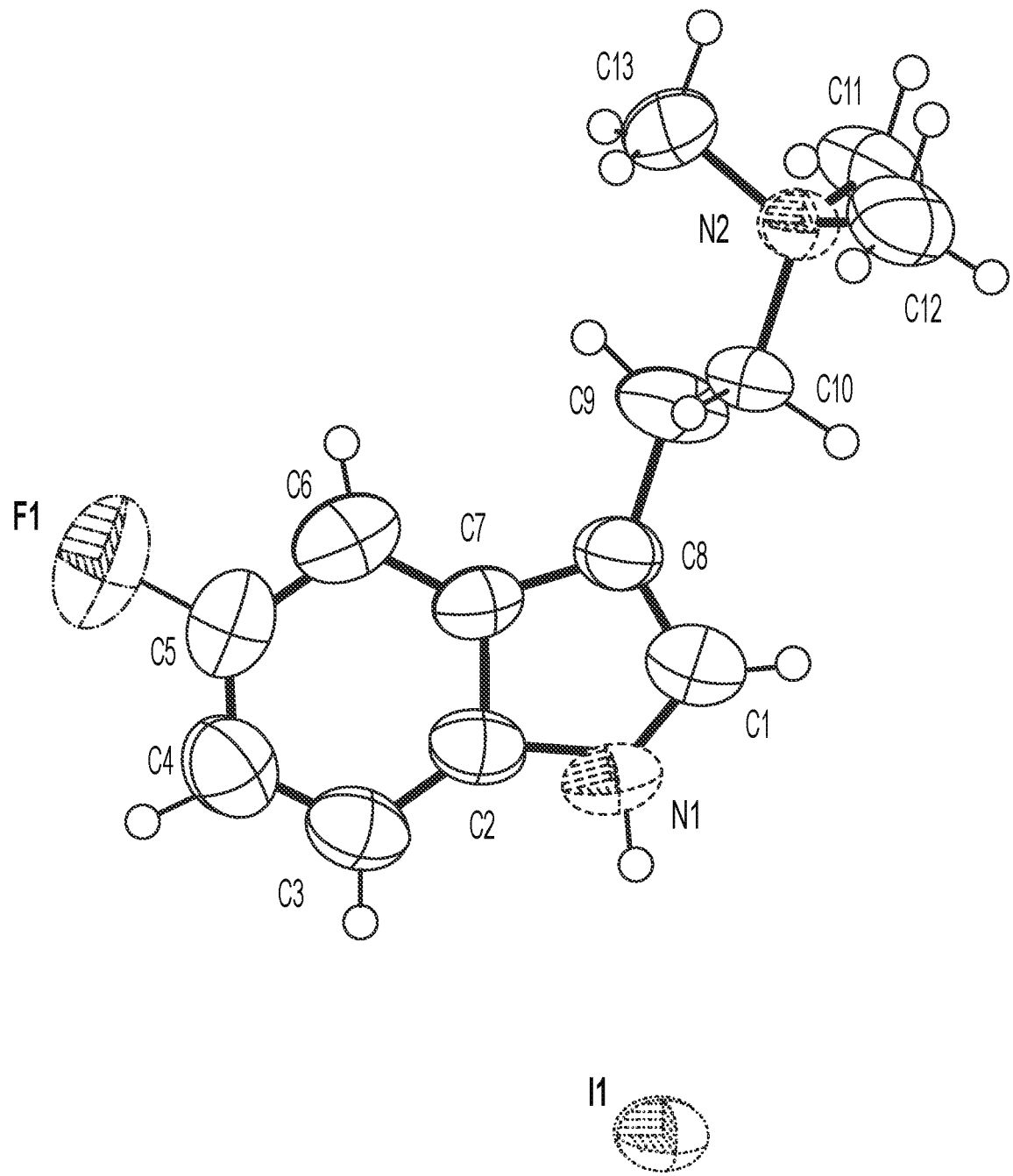
FIG. 1 shows the molecular structure of crystalline 5-fluoro-N,N,N-trimethyltryptammonium (5-F-TMT) iodide, showing the atom labeling.

This disclosure relates to quaternary amine compounds of formula (I):

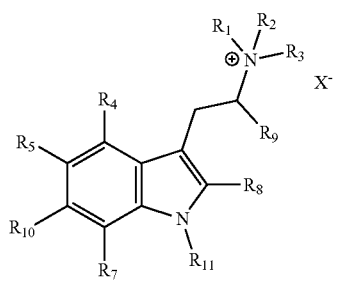

wherein:
$R_1$, $R_2$, and $R_3$ are each independently chosen from a $C_1$-$C_6$ alkyl or $C_2$-$C_6$ alkenyl;
one of $R_4$ and $R_5$ is hydrogen and the other of $R_4$ and $R_5$ is —$OSO_2R_6$;
$R_6$ is a $C_1$-$C_6$ alkyl or a substituted or unsubstituted aryl;
$R_7$, $R_8$, and $R_9$ are each independently hydrogen or $C_1$-$C_6$ alkyl;
$R_{10}$ is selected from hydrogen, $C_1$-$C_6$ alkyl, $C_2$-$C_6$ alkenyl, halogen, hydroxy, —$OR_6$, —$OC(O)R_6$, —$OC(O)OR_6$, or —$OSO_2R_6$;
$R_{11}$ is selected from hydrogen, $C_1$-$C_6$ alkyl, $C_2$-$C_6$ alkenyl, —$C(O)R_6$, —$C(O)OR_6$, or —$SO_2R_6$; and
$X^-$ is a pharmaceutically acceptable anion.

In formula (I), $R_1$, $R_2$, and $R_3$ are each independently chosen from a $C_1$-$C_6$ alkyl, or $C_2$-$C_6$ alkenyl. $R_1$, $R_2$, and $R_3$ may each independently be a straight chain or branched $C_1$-$C_6$ alkyl, for example a straight chain $C_1$-$C_6$ alkyl, or a straight chain or branched $C_2$-$C_6$ alkenyl, for example allyl, 2-butenyl, etc. In some embodiments $R_1$, $R_2$, and $R_3$ may each independently be a straight chain or branched $C_1$-$C_4$ alkyl, for example a straight chain $C_1$-$C_4$ alkyl, or a $C_2$-$C_4$ alkenyl. $R_1$, $R_2$, and $R_3$ may each independently be selected from methyl, ethyl, n-propyl, isopropyl, cyclopropyl, n-butyl, isobutyl, or tert-butyl. In other embodiments, $R_1$, $R_2$, and $R_3$ may each independently be methyl, ethyl, n-propyl, isopropyl, n-butyl, isobutyl, and tert-butyl. In other embodiments, $R_1$, $R_2$, and $R_3$ are each methyl, are each ethyl, or a mixture of methyl and ethyl groups.

In formula (I), one of $R_4$ and $R_5$ is hydrogen and the other of $R_4$ and $R_5$ is —$OSO_2R_6$. $R_6$ is a $C_1$-$C_6$ alkyl or a substituted or unsubstituted aryl. $R_6$ may be a straight chain or branched $C_1$-$C_4$ alkyl, for example a straight chain $C_1$-$C_4$ alkyl. In some embodiments, $R_6$ is selected from methyl, ethyl, n-propyl, or n-butyl, and for example is methyl or ethyl. $R_6$ may also be a substituted or unsubstituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g. F, Cl, I or Br). An aryl group may be ortho-, meta- and/or para-substituted, preferably para-substituted. When an aryl group is substituted with one or more straight chain or branched $C_1$-$C_4$ alkyl perfluoralkyl groups the group may be methyl, trifluoromethyl, ethyl, n-propyl, isopropyl, n-butyl, isobutyl, or tert-butyl or the group may be methyl, ethyl, isopropyl, or tert-butyl. When $R_4$ or $R_5$ is —$OSO_2R_6$, $R_6$ may be a methyl, a tert-butyl, a phenyl, a benzyl, a para-halophenyl or a para-tolyl group.

In formula (I), $R_7$, $R_8$, and $R_9$ are each independently hydrogen or $C_1$-$C_6$ alkyl, for example a straight chain $C_1$-$C_4$ alkyl. In some embodiments, $R_7$, $R_8$, and $R_9$ are each independently selected from hydrogen, methyl, ethyl, n-propyl, isopropyl, n-butyl, and isobutyl. In other embodiments, $R_7$, $R_8$, and $R_9$ are each independently hydrogen, methyl, or ethyl.

In formula (I), $R_{10}$ is selected from hydrogen, $C_1$-$C_6$ alkyl, $C_2$-$C_6$ alkenyl, halogen, hydroxy, —$OR_6$, —$OC(O)R_6$, —$OC(O)OR_6$, or —$OSO_2R_6$. $R_{10}$ may be a straight chain or branched $C_1$-$C_6$ alkyl, for example a straight chain $C_1$-$C_6$ alkyl, or a straight chain or branched $C_2$-$C_6$ alkenyl, for example allyl, 2-butenyl, etc. In some embodiments $R_{10}$ may be a straight chain or branched $C_1$-$C_4$ alkyl, for example a straight chain $C_1$-$C_4$ alkyl, or a $C_2$-$C_4$ alkenyl. $R_{10}$ may be selected from methyl, ethyl, n-propyl, isopropyl, cyclopropyl, n-butyl, isobutyl, or tert-butyl. In other embodiments, $R_{10}$ may be methyl, ethyl, n-propyl, isopropyl, n-butyl, isobutyl, and tert-butyl. $R_{10}$ may be a halogen. Exemplary halogens include fluorine (F), chlorine (Cl), bromine (Br), and iodine (I). In some embodiments, $R_{10}$ may be selected from —$OR_6$, —$OC(O)R_6$, —$OC(O)OR_6$, or —$OSO_2R_6$, wherein $R_6$ is a $C_1$-$C_6$ alkyl or a substituted or unsubstituted aryl. $R_6$ may be a straight chain or branched $C_1$-$C_4$ alkyl, for example a straight chain $C_1$-$C_4$ alkyl. In some embodiments, $R_6$ is selected from methyl, ethyl, n-propyl, or n-butyl, and for example is methyl or ethyl. $R_6$ may also be a substituted or unsubstituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g. F, Cl, I or Br). An aryl group may be ortho-, meta- and/or para-substituted, preferably para-substituted. When an aryl group is substituted with one or more straight chain or branched $C_1$-$C_4$ alkyl perfluoralkyl groups the group may be methyl, trifluoromethyl, ethyl, n-propyl, isopropyl, n-butyl, isobutyl, or tert-butyl or the group may be methyl, ethyl, isopropyl, or tert-butyl. When $R_{10}$ is —$OSO_2R_6$, $R_6$ may be a methyl, a tert-butyl, a phenyl, a benzyl, a para-halophenyl or a para-tolyl group.

In formula (I), $R_{11}$ is selected from hydrogen, $C_1$-$C_6$ alkyl, $C_2$-$C_6$ alkenyl, —$C(O)R_6$, —$C(O)OR_6$, or —$SO_2R_6$. $R_{11}$ may be a straight chain or branched $C_1$-$C_6$ alkyl, for example a straight chain $C_1$-$C_6$ alkyl, or a straight chain or branched $C_2$-$C_6$ alkenyl, for example allyl, 2-butenyl, etc. In some embodiments, $R_{11}$ may be a straight chain or branched $C_1$-$C_4$ alkyl, for example a straight chain $C_1$-$C_4$ alkyl, or a $C_2$-$C_4$ alkenyl. $R_{11}$ may be selected from methyl, ethyl, n-propyl, isopropyl, cyclopropyl, n-butyl, isobutyl, or tert-butyl. In other embodiments, $R_{11}$ may be methyl, ethyl, n-propyl, isopropyl, n-butyl, isobutyl, and tert-butyl. In some embodiments, Ra may be selected from —$C(O)R_6$, —$C(O)OR_6$, or —$SO_2R_6$, wherein $R_6$ is a $C_1$-$C_6$ alkyl or a substituted or unsubstituted aryl. $R_6$ may be a straight chain or branched $C_1$-$C_4$ alkyl, for example a straight chain $C_1$-$C_4$ alkyl. In some embodiments, $R_6$ is selected from methyl, ethyl, n-propyl, or n-butyl, and for example is methyl or ethyl. $R_6$ may also be a substituted or unsubstituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g. F, Cl, I or Br). An aryl group may be ortho-, meta- and/or para-substituted, preferably para-substituted. When an aryl group is substituted with one or more straight chain or branched $C_1$-$C_4$ alkyl perfluoralkyl groups the group may be methyl, trifluoromethyl, ethyl, n-propyl, isopropyl, n-butyl, isobutyl, or tert-butyl or the group may be methyl, ethyl, isopropyl, or tert-butyl.

The anion of formula (I), $X^-$, may be any pharmaceutically acceptable anion, for example, $Cl^-$, $I^-$, $Br^-$, ascorbate, hydrofumarate, fumarate, maleate, and the like. A preferred anion, $X^-$, is iodide, $I^-$. When the pharmaceutically acceptable anion is a di-anion it balances two of the ammonium cations.

A compound of formula (Ia) (below) is reacted with $XR_3$, where $XR_3$ is an alkyl agent, by refluxing in an appropriate organic solvent, such as methanol or THF, under an inert atmosphere, to prepare a compound of formula (I).

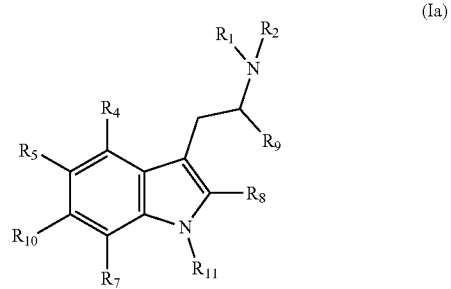

The reaction is shown in the following reaction:

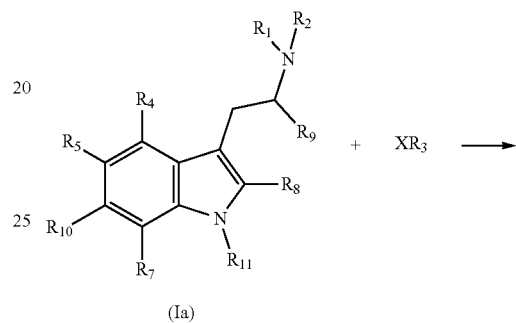

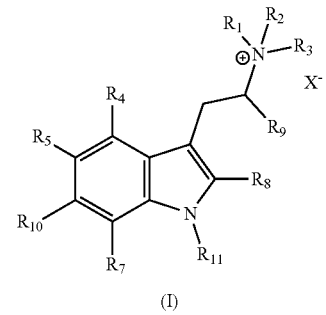

A compound of formula (Ia) is treated with an alkyl agent. For example, the alkyl agent may be an alkyl halide, an alkyl iodide, a methyl iodide, an ethyl iodide, a propyl iodide, or a butyl iodide.

In a preferred embodiment, $XR_3$ is $ICH_3$ or $ICH_2CH_3$. When $R_4$ or $R_5$ of formula (Ia) is hydroxyl it can be converted to —$OSO_2R_6$, as is known in the art. Hydroxyl groups may be introduced by hydrolysis of a corresponding ester. Other pharmaceutically acceptable salts may be prepared by anion exchange techniques known in the art to exchange the iodide anion for a desired pharmaceutically acceptable anion. For example, the iodide anion may be exchanged using an anion exchange resin.

Exemplary compounds prepared by the above reaction can be found in Tables 1 and 2. Table 1 contains the exemplary reactants and Table 2 contains the corresponding products.

TABLE 1

Reactants

| Compound | Formula (Ia) ($R_7$, $R_8$, $R_9$, $R_{10}$, and $R_{11}$ are H) | | | | $XR_3$ |
|---|---|---|---|---|---|
| | $R_1$ | $R_2$ | $R_4$ | $R_5$ | $XR_3$ |
| 1 | —$CH_2CH_2CH_3$ | —$CH_2CH_2CH_3$ | —$OSO_2CH_3$ | —H | —$ICH_3$ |
| 2 | —$CH_2CH_2CH_3$ | —$CH_2CH_2CH_3$ | —$OSO_2CH_3$ | —H | —$ICH_2CH_3$ |

TABLE 1-continued

Reactants

| | Formula (Ia) ($R_7$, $R_8$, $R_9$, $R_{10}$, and $R_{11}$ are H) | | | | $XR_3$ |
|---|---|---|---|---|---|
| Compound | $R_1$ | $R_2$ | $R_4$ | $R_5$ | $XR_3$ |
| 3 | —$CH_2CH_2CH_3$ | —$CH_2CH_2CH_3$ | —$OSO_2CH_3$ | —H | —$ICH_2CH_2CH_3$ |
| 4 | —$CH_2CH_2CH_3$ | —$CH_2CH_2CH_3$ | —$OSO_2CH_3$ | —H | —$ICH_2CH_2CH_2CH_3$ |
| 5 | —$CH_2CH_2CH_3$ | —$CH_2CH_2CH_3$ | —$OSO_2CH_2CH_3$ | —H | —$ICH_3$ |
| 6 | —$CH_2CH_2CH_3$ | —$CH_2CH_2CH_3$ | —$OSO_2CH_2CH_3$ | —H | —$ICH_2CH_3$ |
| 7 | —$CH_2CH_2CH_3$ | —$CH_2CH_2CH_3$ | —$OSO_2CH_2CH_3$ | —H | —$ICH_2CH_2CH_3$ |
| 8 | —$CH_2CH_2CH_3$ | —$CH_2CH_2CH_3$ | —$OSO_2CH_2CH_3$ | —H | —$ICH_2CH_2CH_2CH_3$ |
| 9 | —$CH_2CH_2CH_3$ | —$CH_2CH_2CH_3$ | —$OSO_2CH_2CH_2CH_3$ | —H | —$ICH_3$ |
| 10 | —$CH_2CH_2CH_3$ | —$CH_2CH_2CH_3$ | —$OSO_2CH_2CH_2CH_3$ | —H | —$ICH_2CH_3$ |
| 11 | —$CH_2CH_2CH_3$ | —$CH_2CH_2CH_3$ | —$OSO_2CH_2CH_2CH_3$ | —H | —$ICH_2CH_2CH_3$ |
| 12 | —$CH_2CH_2CH_3$ | —$CH_2CH_2CH_3$ | —$OSO_2CH_2CH_2CH_3$ | —H | —$ICH_2CH_2CH_2CH_3$ |
| 13 | —$CH_2CH_2CH_3$ | —$CH_2CH_2CH_3$ | —$OSO_2C_6H_5$ | —H | —$ICH_3$ |
| 14 | —$CH_2CH_2CH_3$ | —$CH_2CH_2CH_3$ | —$OSO_2C_6H_5$ | —H | —$ICH_2CH_3$ |
| 15 | —$CH_2CH_2CH_3$ | —$CH_2CH_2CH_3$ | —$OSO_2C_6H_5$ | —H | —$ICH_2CH_2CH_3$ |
| 16 | —$CH_2CH_2CH_3$ | —$CH_2CH_2CH_3$ | —$OSO_2C_6H_5$ | —H | —$ICH_2CH_2CH_2CH_3$ |
| 17 | —$CH_2CH_2CH_3$ | —$CH_2CH_2CH_3$ | —$OSO_2C_6H_4CH_3$ | —H | —$ICH_3$ |
| 18 | —$CH_2CH_2CH_3$ | —$CH_2CH_2CH_3$ | —$OSO_2C_6H_4CH_3$ | —H | —$ICH_2CH_3$ |
| 19 | —$CH_2CH_2CH_3$ | —$CH_2CH_2CH_3$ | —$OSO_2C_6H_4CH_3$ | —H | —$ICH_2CH_2CH_3$ |
| 20 | —$CH_2CH_2CH_3$ | —$CH_2CH_2CH_3$ | —$OSO_2C_6H_4CH_3$ | —H | —$ICH_2CH_2CH_2CH_3$ |
| 21 | —$CH_2CH_2CH_3$ | —$CH_2CH_2CH_3$ | —$OSO_2C_6H_4CF_3$ | —H | —$ICH_3$ |
| 22 | —$CH_2CH_2CH_3$ | —$CH_2CH_2CH_3$ | —$OSO_2C_6H_4CF_3$ | —H | —$ICH_2CH_3$ |
| 23 | —$CH_2CH_2CH_3$ | —$CH_2CH_2CH_3$ | —$OSO_2C_6H_4CF_3$ | —H | —$ICH_2CH_2CH_3$ |
| 24 | —$CH_2CH_2CH_3$ | —$CH_2CH_2CH_3$ | —$OSO_2C_6H_4CF_3$ | —H | —$ICH_2CH_2CH_2CH_3$ |
| 25 | —$CH_2CH_2CH_3$ | —$CH_2CH_2CH_3$ | —$OSO_2C_6H_4NO_2$ | —H | —$ICH_3$ |
| 26 | —$CH_2CH_2CH_3$ | —$CH_2CH_2CH_3$ | —$OSO_2C_6H_4NO_2$ | —H | —$ICH_2CH_3$ |
| 27 | —$CH_2CH_2CH_3$ | —$CH_2CH_2CH_3$ | —$OSO_2C_6H_4NO_2$ | —H | —$ICH_2CH_2CH_3$ |
| 28 | —$CH_2CH_2CH_3$ | —$CH_2CH_2CH_3$ | —$OSO_2C_6H_4NO_2$ | —H | —$ICH_2CH_2CH_2CH_3$ |
| 29 | —$CH_2CH_2CH_3$ | —$CH_2CH_2CH_3$ | —$OSO_2C_6H_4Cl$ | —H | —$ICH_3$ |
| 30 | —$CH_2CH_2CH_3$ | —$CH_2CH_2CH_3$ | —$OSO_2C_6H_4Cl$ | —H | —$ICH_2CH_3$ |
| 31 | —$CH_2CH_2CH_3$ | —$CH_2CH_2CH_3$ | —$OSO_2C_6H_4Cl$ | —H | —$ICH_2CH_2CH_3$ |
| 32 | —$CH_2CH_2CH_3$ | —$CH_2CH_2CH_3$ | —$OSO_2C_6H_4Cl$ | —H | —$ICH_2CH_2CH_2CH_3$ |
| 33 | —$CH_2CH_2CH_3$ | —$CH_2CH_2CH_3$ | —$OSO_2C_6H_4Br$ | —H | —$ICH_3$ |
| 34 | —$CH_2CH_2CH_3$ | —$CH_2CH_2CH_3$ | —$OSO_2C_6H_4Br$ | —H | —$ICH_2CH_3$ |
| 35 | —$CH_2CH_2CH_3$ | —$CH_2CH_2CH_3$ | —$OSO_2C_6H_4Br$ | —H | —$ICH_2CH_2CH_3$ |
| 36 | —$CH_2CH_2CH_3$ | —$CH_2CH_2CH_3$ | —$OSO_2C_6H_4Br$ | —H | —$ICH_2CH_2CH_2CH_3$ |
| 37 | —$CH_2CH_2CH_3$ | —$CH_2CH_2CH_3$ | —$OSO_2C_6H_4F$ | —H | —$ICH_3$ |
| 38 | —$CH_2CH_2CH_3$ | —$CH_2CH_2CH_3$ | —$OSO_2C_6H_4F$ | —H | —$ICH_2CH_3$ |
| 39 | —$CH_2CH_2CH_3$ | —$CH_2CH_2CH_3$ | —$OSO_2C_6H_4F$ | —H | —$ICH_2CH_2CH_3$ |
| 40 | —$CH_2CH_2CH_3$ | —$CH_2CH_2CH_3$ | —$OSO_2C_6H_4F$ | —H | —$ICH_2CH_2CH_2CH_3$ |

TABLE 2

Products

| | Formula (I) ($R_7$, $R_8$, $R_9$, $R_{10}$, and $R_{11}$ are H) | | | | | |
|---|---|---|---|---|---|---|
| Compound | $R_1$ | $R_2$ | $R_3$ | $R_4$ | $R_5$ | $X^-$ |
| 1 | —$CH_2CH_2CH_3$ | —$CH_2CH_2CH_3$ | —$CH_3$ | —$OSO_2CH_3$ | —H | —$I^-$ |
| 2 | —$CH_2CH_2CH_3$ | —$CH_2CH_2CH_3$ | —$CH_2CH_3$ | —$OSO_2CH_3$ | —H | —$I^-$ |
| 3 | —$CH_2CH_2CH_3$ | —$CH_2CH_2CH_3$ | —$CH_2CH_2CH_3$ | —$OSO_2CH_3$ | —H | —$I^-$ |
| 4 | —$CH_2CH_2CH_3$ | —$CH_2CH_2CH_3$ | —$CH_2CH_2CH_2CH_3$ | —$OSO_2CH_3$ | —H | —$I^-$ |
| 5 | —$CH_2CH_2CH_3$ | —$CH_2CH_2CH_3$ | —$CH_3$ | —$OSO_2CH_2CH_3$ | —H | —$I^-$ |
| 6 | —$CH_2CH_2CH_3$ | —$CH_2CH_2CH_3$ | —$CH_2CH_3$ | —$OSO_2CH_2CH_3$ | —H | —$I^-$ |
| 7 | —$CH_2CH_2CH_3$ | —$CH_2CH_2CH_3$ | —$CH_2CH_2CH_3$ | —$OSO_2CH_2CH_3$ | —H | —$I^-$ |
| 8 | —$CH_2CH_2CH_3$ | —$CH_2CH_2CH_3$ | —$CH_2CH_2CH_2CH_3$ | —$OSO_2CH_2CH_3$ | —H | —$I^-$ |
| 9 | —$CH_2CH_2CH_3$ | —$CH_2CH_2CH_3$ | —$CH_3$ | —$OSO_2CH_2CH_2CH_3$ | —H | —$I^-$ |
| 10 | —$CH_2CH_2CH_3$ | —$CH_2CH_2CH_3$ | —$CH_2CH_3$ | —$OSO_2CH_2CH_2CH_3$ | —H | —$I^-$ |
| 11 | —$CH_2CH_2CH_3$ | —$CH_2CH_2CH_3$ | —$CH_2CH_2CH_3$ | —$OSO_2CH_2CH_2CH_3$ | —H | —$I^-$ |
| 12 | —$CH_2CH_2CH_3$ | —$CH_2CH_2CH_3$ | —$CH_2CH_2CH_2CH_3$ | —$OSO_2CH_2CH_2CH_3$ | —H | —$I^-$ |
| 13 | —$CH_2CH_2CH_3$ | —$CH_2CH_2CH_3$ | —$CH_3$ | —$OSO_2C_6H_5$ | —H | —$I^-$ |
| 14 | —$CH_2CH_2CH_3$ | —$CH_2CH_2CH_3$ | —$CH_2CH_3$ | —$OSO_2C_6H_5$ | —H | —$I^-$ |
| 15 | —$CH_2CH_2CH_3$ | —$CH_2CH_2CH_3$ | —$CH_2CH_2CH_3$ | —$OSO_2C_6H_5$ | —H | —$I^-$ |
| 16 | —$CH_2CH_2CH_3$ | —$CH_2CH_2CH_3$ | —$CH_2CH_2CH_2CH_3$ | —$OSO_2C_6H_5$ | —H | —$I^-$ |
| 17 | —$CH_2CH_2CH_3$ | —$CH_2CH_2CH_3$ | —$CH_3$ | —$OSO_2C_6H_4CH_3$ | —H | —$I^-$ |
| 18 | —$CH_2CH_2CH_3$ | —$CH_2CH_2CH_3$ | —$CH_2CH_3$ | —$OSO_2C_6H_4CH_3$ | —H | —$I^-$ |
| 19 | —$CH_2CH_2CH_3$ | —$CH_2CH_2CH_3$ | —$CH_2CH_2CH_3$ | —$OSO_2C_6H_4CH_3$ | —H | —$I^-$ |
| 20 | —$CH_2CH_2CH_3$ | —$CH_2CH_2CH_3$ | —$CH_2CH_2CH_2CH_3$ | —$OSO_2C_6H_4CH_3$ | —H | —$I^-$ |
| 21 | —$CH_2CH_2CH_3$ | —$CH_2CH_2CH_3$ | —$CH_3$ | —$OSO_2C_6H_4CF_3$ | —H | —$I^-$ |
| 22 | —$CH_2CH_2CH_3$ | —$CH_2CH_2CH_3$ | —$CH_2CH_3$ | —$OSO_2C_6H_4CF_3$ | —H | —$I^-$ |
| 23 | —$CH_2CH_2CH_3$ | —$CH_2CH_2CH_3$ | —$CH_2CH_2CH_3$ | —$OSO_2C_6H_4CF_3$ | —H | —$I^-$ |

TABLE 2-continued

Products

Formula (I) ($R_7$, $R_8$, $R_9$, $R_{10}$, and $R_{11}$ are H)

| Compound | $R_1$ | $R_2$ | $R_3$ | $R_4$ | $R_5$ | $X^-$ |
|---|---|---|---|---|---|---|
| 24 | —CH$_2$CH$_2$CH$_3$ | —CH$_2$CH$_2$CH$_3$ | —CH$_2$CH$_2$CH$_2$CH$_3$ | —OSO$_2$C$_6$H$_4$CF$_3$ | —H | —I$^-$ |
| 25 | —CH$_2$CH$_2$CH$_3$ | —CH$_2$CH$_2$CH$_3$ | —CH$_3$ | —OSO$_2$C$_6$H$_4$NO$_2$ | —H | —I$^-$ |
| 26 | —CH$_2$CH$_2$CH$_3$ | —CH$_2$CH$_2$CH$_3$ | —CH$_2$CH$_3$ | —OSO$_2$C$_6$H$_4$NO$_2$ | —H | —I$^-$ |
| 27 | —CH$_2$CH$_2$CH$_3$ | —CH$_2$CH$_2$CH$_3$ | —CH$_2$CH$_2$CH$_3$ | —OSO$_2$C$_6$H$_4$NO$_2$ | —H | —I$^-$ |
| 28 | —CH$_2$CH$_2$CH$_3$ | —CH$_2$CH$_2$CH$_3$ | —CH$_2$CH$_2$CH$_2$CH$_3$ | —OSO$_2$C$_6$H$_4$NO$_2$ | —H | —I$^-$ |
| 29 | —CH$_2$CH$_2$CH$_3$ | —CH$_2$CH$_2$CH$_3$ | —CH$_3$ | —OSO$_2$C$_6$H$_4$Cl | —H | —I$^-$ |
| 30 | —CH$_2$CH$_2$CH$_3$ | —CH$_2$CH$_2$CH$_3$ | —CH$_2$CH$_3$ | —OSO$_2$C$_6$H$_4$Cl | —H | —I$^-$ |
| 31 | —CH$_2$CH$_2$CH$_3$ | —CH$_2$CH$_2$CH$_3$ | —CH$_2$CH$_2$CH$_3$ | —OSO$_2$C$_6$H$_4$Cl | —H | —I$^-$ |
| 32 | —CH$_2$CH$_2$CH$_3$ | —CH$_2$CH$_2$CH$_3$ | —CH$_2$CH$_2$CH$_2$CH$_3$ | —OSO$_2$C$_6$H$_4$Cl | —H | —I$^-$ |
| 33 | —CH$_2$CH$_2$CH$_3$ | —CH$_2$CH$_2$CH$_3$ | —CH$_3$ | —OSO$_2$C$_6$H$_4$Br | —H | —I$^-$ |
| 34 | —CH$_2$CH$_2$CH$_3$ | —CH$_2$CH$_2$CH$_3$ | —CH$_2$CH$_3$ | —OSO$_2$C$_6$H$_4$Br | —H | —I$^-$ |
| 35 | —CH$_2$CH$_2$CH$_3$ | —CH$_2$CH$_2$CH$_3$ | —CH$_2$CH$_2$CH$_3$ | —OSO$_2$C$_6$H$_4$Br | —H | —I$^-$ |
| 36 | —CH$_2$CH$_2$CH$_3$ | —CH$_2$CH$_2$CH$_3$ | —CH$_2$CH$_2$CH$_2$CH$_3$ | —OSO$_2$C$_6$H$_4$Br | —H | —I$^-$ |
| 37 | —CH$_2$CH$_2$CH$_3$ | —CH$_2$CH$_2$CH$_3$ | —CH$_3$ | —OSO$_2$C$_6$H$_4$F | —H | —I$^-$ |
| 38 | —CH$_2$CH$_2$CH$_3$ | —CH$_2$CH$_2$CH$_3$ | —CH$_2$CH$_3$ | —OSO$_2$C$_6$H$_4$F | —H | —I$^-$ |
| 39 | —CH$_2$CH$_2$CH$_3$ | —CH$_2$CH$_2$CH$_3$ | —CH$_2$CH$_2$CH$_3$ | —OSO$_2$C$_6$H$_4$F | —H | —I$^-$ |
| 40 | —CH$_2$CH$_2$CH$_3$ | —CH$_2$CH$_2$CH$_3$ | —CH$_2$CH$_2$CH$_2$CH$_3$ | —OSO$_2$C$_6$H$_4$F | —H | —I$^-$ |

This disclosure also relates to a compound of formula (II):

(II)

wherein:

$R_1$, $R_2$, and $R_3$ are each independently a straight chain or branched $C_1$-$C_6$ alkyl or $C_2$-$C_6$ alkenyl;

$R_4$ is hydrogen, hydroxy, —OR$_5$, —OC(O)R$_5$, —OC(O)OR$_5$, or —OSO$_2$R$_5$;

$R_5$ is a straight chain or branched $C_1$-$C_6$ alkyl or a substituted or unsubstituted aryl;

$R_6$ is a halogen chosen from F, Cl, Br, and I; and $R_7$, $R_8$, $R_9$, and $R_{10}$ are each independently hydrogen or a straight chain or branched $C_1$-$C_6$ alkyl;

$R_{11}$ is selected from hydrogen, $C_1$-$C_6$ alkyl, $C_2$-$C_6$ alkenyl, —C(O)R$_5$, —C(O)OR$_5$, or —SO$_2$R$_5$; and $X^-$ is a pharmaceutically acceptable anion.

In formula (II), $R_1$, $R_2$, and $R_3$ are each independently a straight chain or branched $C_1$-$C_6$ alkyl or $C_2$-$C_6$ alkenyl, such as a straight-chained $C_1$-$C_6$ alkyl (e.g., methyl, ethyl, n-propyl). In some embodiments, $R_1$, $R_2$, and $R_3$ are each independently a straight chain or branched $C_2$-$C_6$ alkyl or $C_3$-$C_6$ alkyl. In some embodiments, $R_1$, $R_2$, and $R_3$ are each independently selected from methyl, ethyl, n-propyl, isopropyl, n-butyl, tert-butyl, and isobutyl.

In formula (II), $R_4$ is hydrogen, hydroxy, —OR$_5$, —OC(O)R$_5$, —OC(O)OR$_5$, or —OSO$_2$R$_5$. When $R_4$ is $C_1$-$C_6$ alkoxy group, or in some embodiments a $C_1$-$C_4$ alkoxy group, it may be a straight chain or branched $C_1$-$C_6$ alkoxy group or $C_1$-$C_4$ alkoxy group, for example a straight chain, and may be methoxy or ethoxy. $R_5$ is a straight chain or branched $C_1$-$C_6$ alkyl or a substituted or unsubstituted aryl. When $R_5$ is a straight chain or branched $C_1$-$C_6$ alkyl, it may be a straight chain or branched $C_1$-$C_4$ alkyl, for example a straight chain $C_1$-$C_4$ alkyl. In some embodiments, $R_5$ is selected from methyl, ethyl, n-propyl or n-butyl, and for example is methyl or ethyl. $R_5$ may also be a substituted or unsubstituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl and phenantherenyl. An aryl group may be substituted with one or more straight chain or branched $C_1$-$C_4$ alkyl groups, straight chain or branched $C_1$-$C_4$ hydroxyalkyl groups, hydroxyl groups or halo groups (e.g. F, Cl, I or Br). When an aryl group is substituted with one or more straight chain or branched $C_1$-$C_4$ alkyl groups the group may be methyl, ethyl, n-propyl, isopropyl, n-butyl, isobutyl or tert-butyl or the group may be methyl, ethyl, isopropyl, or tert-butyl. When $R_4$ is —OR$_5$, —OC(O)R$_5$, —OC(O)OR$_5$, or —OSO$_2$R$_5$, $R_5$ may be a methyl, a tert-butyl, a phenyl or a para-tolyl group.

In formula (II), $R_6$ is a halogen. Exemplary halogens include fluorine (F), chlorine (Cl), bromine (Br), and iodine (I).

$R_7$, $R_8$, $R_9$, and $R_{10}$ in formula (II) are each independently hydrogen or a straight chain or branched $C_1$-$C_4$ alkyl, for example a straight chain $C_1$-$C_4$ alkyl. In some embodiments, $R_7$, $R_8$, $R_9$, and $R_{10}$ are each independently selected from $C_2$-$C_6$ alkyl or $C_3$-$C_6$ alkyl. In some embodiments, $R_7$, $R_8$, $R_9$, and $R_{10}$ are each independently selected from hydrogen, methyl, ethyl, n-propyl, isopropyl, n-butyl, tert-butyl, and isobutyl. In other embodiments, $R_7$, $R_8$, $R_9$, and $R_{10}$ are each independently hydrogen, methyl, or ethyl.

In formula (II), $R_{11}$ is selected from hydrogen, $C_1$-$C_6$ alkyl, $C_2$-$C_6$ alkenyl, —C(O)R$_5$, —C(O)OR$_5$, or —SO$_2$R$_5$. $R_{11}$ may be a straight chain or branched $C_1$-$C_6$ alkyl, for example a straight chain $C_1$-$C_6$ alkyl, or a straight chain or branched $C_2$-$C_6$ alkenyl, for example allyl, 2-butenyl, etc. In some embodiments, $R_{11}$ may be a straight chain or branched $C_1$-$C_4$ alkyl, for example a straight chain $C_1$-$C_4$ alkyl, or a $C_2$-$C_4$ alkenyl. $R_{11}$ may be selected from methyl, ethyl, n-propyl, isopropyl, cyclopropyl, n-butyl, isobutyl, or tert-butyl. In other embodiments, $R_{11}$ may be methyl, ethyl, n-propyl, isopropyl, n-butyl, isobutyl, and tert-butyl. In some embodiments, $R_{11}$ may be selected from —C(O)R$_5$, —C(O)OR$_5$, or —SO$_2$R$_5$, wherein $R_5$ is a straight chain or branched C$_1$-C$_6$ alkyl or a substituted or unsubstituted aryl. When $R_5$ is a straight chain or branched C$_1$-C$_6$ alkyl, it may be a straight chain or branched C$_1$-C$_4$ alkyl, for example a straight chain C$_1$-C$_4$ alkyl. In some embodiments, $R_5$ is selected from methyl, ethyl, n-propyl or n-butyl, and for example is methyl or ethyl. $R_5$ may also be a substituted or unsubstituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl and phenantherenyl. An aryl group may be substituted with one or more straight chain or branched C$_1$-C$_4$ alkyl groups, straight chain or branched C$_1$-C$_4$ hydroxyalkyl groups, hydroxyl groups or halo groups (e.g. F, Cl, I or Br). When an aryl group is substituted with one or more straight chain or branched C$_1$-C$_4$ alkyl groups the group may be methyl, ethyl, n-propyl, isopropyl, n-butyl, isobutyl or tert-butyl or the group may be methyl, ethyl, isopropyl, or tert-butyl.

In one embodiment, formula (II) contains the proviso that when $R_1$, $R_2$, and $R_3$ are methyl and $R_4$, $R_7$, $R_8$, $R_9$, $R_{10}$, and $R_{11}$ are hydrogen, $R_6$ is not Br.

In one embodiment of the compound of formula (II), $R_1$, $R_2$, and $R_3$ are each independently a straight chain or branched C$_1$-C$_6$ alkyl.

In one embodiment of the compound of formula (II), $R_1$ is a straight chain or branched C$_1$-C$_6$ alkyl.

In one embodiment of the compound of formula (II), $R_1$ is a straight chain or branched C$_2$-C$_6$ alkyl.

In one embodiment of the compound of formula (II), $R_1$ is a straight chain or branched C$_3$-C$_6$ alkyl.

In one embodiment of the compound of formula (II), $R_2$ is a straight chain or branched C$_1$-C$_6$ alkyl.

In one embodiment of the compound of formula (II), $R_2$ is a straight chain or branched C$_2$-C$_6$ alkyl.

In one embodiment of the compound of formula (II), $R_2$ is a straight chain or branched C$_3$-C$_6$ alkyl.

In one embodiment of the compound of formula (II), $R_3$ is a straight chain or branched C$_1$-C$_6$ alkyl.

In one embodiment of the compound of formula (II), $R_3$ is a straight chain or branched C$_2$-C$_6$ alkyl.

In one embodiment of the compound of formula (II), $R_3$ is a straight chain or branched C$_3$-C$_6$ alkyl.

In one embodiment of the compound of formula (II), one or more of $R_1$, $R_2$, and $R_3$ is C$_2$-C$_6$ alkenyl.

In one embodiment of the compound of formula (II), $R_4$ is hydrogen.

In one embodiment of the compound of formula (II), $R_4$ is hydroxy.

In one embodiment of the compound of formula (II), $R_4$ is —OR$_5$.

In one embodiment of the compound of formula (II), $R_4$ is —OC(O)R$_5$.

In one embodiment of the compound of formula (II), $R_4$ is —OC(O)OR$_5$.

In one embodiment of the compound of formula (II), $R_4$ is —OSO$_2$R$_5$.

In one embodiment of the compound of formula (II), $R_6$ is chloro.

In one embodiment of the compound of formula (II), $R_6$ is bromo.

In one embodiment of the compound of formula (II), $R_6$ is iodo.

In one embodiment of the compound of formula (II), $R_6$ is fluoro.

In one embodiment of the compound of formula (II), $R_7$ is hydrogen.

In one embodiment of the compound of formula (II), $R_7$ is a straight chain or branched C$_1$-C$_6$ alkyl.

In one embodiment of the compound of formula (II), $R_7$ is a straight chain or branched C$_2$-C$_6$ alkyl.

In one embodiment of the compound of formula (II), $R_7$ is a straight chain or branched C$_3$-C$_6$ alkyl.

In one embodiment of the compound of formula (II), $R_8$ is hydrogen.

In one embodiment of the compound of formula (II), $R_8$ is a straight chain or branched C$_1$-C$_6$ alkyl.

In one embodiment of the compound of formula (II), $R_8$ is a straight chain or branched C$_2$-C$_6$ alkyl.

In one embodiment of the compound of formula (II), $R_8$ is a straight chain or branched C$_3$-C$_6$ alkyl.

In one embodiment of the compound of formula (II), $R_9$ is hydrogen.

In one embodiment of the compound of formula (II), $R_9$ is a straight chain or branched C$_1$-C$_6$ alkyl.

In one embodiment of the compound of formula (II), $R_9$ is a straight chain or branched C$_2$-C$_6$ alkyl.

In one embodiment of the compound of formula (II), $R_9$ is a straight chain or branched C$_3$-C$_6$ alkyl.

In one embodiment of the compound of formula (II), two of $R_1$, $R_2$, and $R_3$ are the same.

In one embodiment of the compound of formula (II), $R_1$, $R_2$, and $R_3$ are the same.

In one embodiment of the compound of formula (II), X$^-$ is iodo.

In one embodiment of the compound of formula (II), each of $R_1$, $R_2$, and $R_3$ is independently selected from straight chain or branched C$_3$-C$_6$ alkyl; $R_4$ is hydrogen; $R_6$ is selected from chloro, iodo, bromo, and fluoro; and each of $R_7$, $R_8$, and $R_9$ is hydrogen. In one embodiment, each of $R_1$, $R_2$, and $R_3$ is propyl. In one embodiment of the compound of formula (II), X$^-$ is iodo.

In one embodiment of the compound of formula (II), each of $R_1$, $R_2$, and $R_3$ is independently selected from straight chain or branched C$_2$-C$_6$ alkyl; $R_4$ is hydrogen; $R_6$ is selected from chloro, iodo, bromo, and fluoro; and each of $R_7$, $R_8$, and $R_9$ is hydrogen. In one embodiment, each of $R_1$, $R_2$, and $R_3$ is ethyl. In one embodiment of the compound of formula (II), X$^-$ is iodo.

In one embodiment of the compound of formula (II), each of $R_1$, $R_2$, and $R_3$ is methyl; $R_4$ is hydrogen; $R_6$ is selected from chloro, iodo, and fluoro; and each of $R_7$, $R_8$, and $R_9$ is hydrogen. In one embodiment of the compound of formula (II), X$^-$ is iodo.

Pharmaceutically acceptable salts for a compound of formula (II) may be any acid (e.g. HX or H$_2$X) addition salts. The anion, X$^-$, may be any pharmaceutically acceptable anion, for example, Cl$^-$, I$^-$, B$^-$, ascorbate, hydrofumarate, fumarate, maleate, and the like. When the pharmaceutically acceptable anion is a di-anion it balances two of the ammonium cations. Other pharmaceutically acceptable salts may be prepared by anion exchange techniques known in the art to exchange the iodide anion for a desired pharmaceutically acceptable anion. For example, the iodide anion may be exchanged using an anion exchange resin.

A compound of formula (II) may be prepared by a variety of methods known in the organic synthesis art. In some cases, compounds of formula (II) may be prepared by treating a 5-halo tryptamine with excess alkyl halide.

A compound of formula (IIa) (below) is reacted with XR$_3$, where XR$_3$ is an alkyl halide, by refluxing in an appropriate organic solvent, such as isopropanol, under an inert atmosphere, to prepare a compound of formula (II).

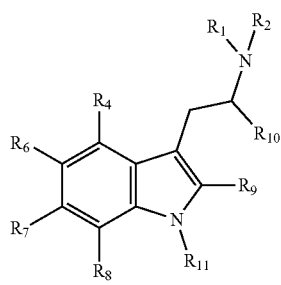

(IIa)

The reaction is shown in the following reaction:

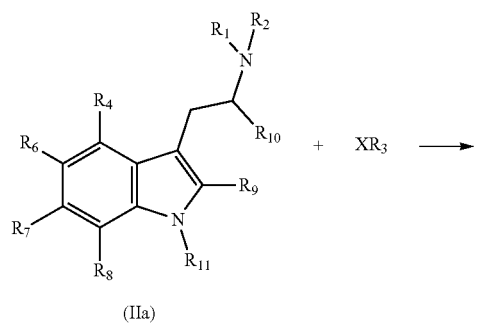

(IIa)

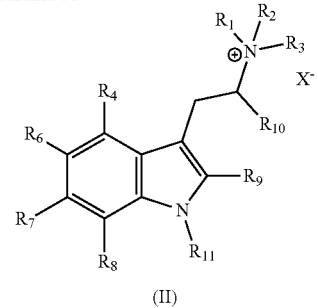

(II)

A compound of formula (IIa) is treated with an alkyl halide. For example, the alkyl halide may be an alkyl iodide, a methyl iodide, an ethyl iodide, a propyl iodide, or a butyl iodide.

In a preferred embodiment, XR$_3$ is ICH$_3$, ICH$_2$CH$_3$, or ICH$_2$CH$_2$CH$_3$. Other pharmaceutically acceptable salts may be prepared by anion exchange techniques known in the art to exchange the iodide anion for a desired pharmaceutically acceptable anion. For example, the iodide anion may be exchanged using an anion exchange resin.

Exemplary compounds prepared by the above reaction can be found in Tables 3 and 4. Table 3 contains the exemplary reactants and Table 4 contains the corresponding products.

TABLE 3

Reactants

Formula (IIa) ($R_4$, $R_7$, $R_8$, $R_9$, $R_{10}$, and $R_{11}$ are H)   XR$_3$

| Compound | $R_1$ | $R_2$ | $R_6$ | XR$_3$ |
|---|---|---|---|---|
| 1 | —CH$_3$ | —CH$_3$ | —F | —ICH$_3$ |
| 2 | —CH$_2$CH$_3$ | —CH$_2$CH$_3$ | —F | —ICH$_2$CH$_3$ |
| 3 | —CH$_2$CH$_2$CH$_3$ | —CH$_2$CH$_2$CH$_3$ | —F | —ICH$_2$CH$_2$CH$_3$ |
| 4 | —CH$_2$CH$_2$CH$_2$CH$_3$ | —CH$_2$CH$_2$CH$_2$CH$_3$ | —F | —ICH$_2$CH$_2$CH$_2$CH$_3$ |
| 5 | —CH$_3$ | —CH$_3$ | —Cl | —ICH$_3$ |
| 6 | —CH$_2$CH$_3$ | —CH$_2$CH$_3$ | —Cl | —ICH$_2$CH$_3$ |
| 7 | —CH$_2$CH$_2$CH$_3$ | —CH$_2$CH$_2$CH$_3$ | —Cl | —ICH$_2$CH$_2$CH$_3$ |
| 8 | —CH$_2$CH$_2$CH$_2$CH$_3$ | —CH$_2$CH$_2$CH$_2$CH$_3$ | —Cl | —ICH$_2$CH$_2$CH$_2$CH$_3$ |
| 9 | —CH$_3$ | —CH$_3$ | —Br | —ICH$_3$ |
| 10 | —CH$_2$CH$_3$ | —CH$_2$CH$_3$ | —Br | —ICH$_2$CH$_3$ |
| 11 | —CH$_2$CH$_2$CH$_3$ | —CH$_2$CH$_2$CH$_3$ | —Br | —ICH$_2$CH$_2$CH$_3$ |
| 12 | —CH$_2$CH$_2$CH$_2$CH$_3$ | —CH$_2$CH$_2$CH$_2$CH$_3$ | —Br | —ICH$_2$CH$_2$CH$_2$CH$_3$ |
| 13 | —CH$_3$ | —CH$_3$ | —I | —ICH$_3$ |
| 14 | —CH$_2$CH$_3$ | —CH$_2$CH$_3$ | —I | —ICH$_2$CH$_3$ |
| 15 | —CH$_2$CH$_2$CH$_3$ | —CH$_2$CH$_2$CH$_3$ | —I | —ICH$_2$CH$_2$CH$_3$ |
| 16 | —CH$_2$CH$_2$CH$_2$CH$_3$ | —CH$_2$CH$_2$CH$_2$CH$_3$ | —I | —ICH$_2$CH$_2$CH$_2$CH$_3$ |

TABLE 4

Products

Formula (II) ($R_4$, $R_7$, $R_8$, $R_9$, $R_{10}$, and $R_{11}$ are H)

| Compound | $R_1$ | $R_2$ | $R_3$ | $R_6$ | $X^-$ |
|---|---|---|---|---|---|
| 1 | —CH$_3$ | —CH$_3$ | —CH$_3$ | —F | —I$^-$ |
| 2 | —CH$_2$CH$_3$ | —CH$_2$CH$_3$ | —CH$_2$CH$_3$ | —F | —I$^-$ |
| 3 | —CH$_2$CH$_2$CH$_3$ | —CH$_2$CH$_2$CH$_3$ | —CH$_2$CH$_2$CH$_3$ | —F | —I$^-$ |
| 4 | —CH$_2$CH$_2$CH$_2$CH$_3$ | —CH$_2$CH$_2$CH$_2$CH$_3$ | —CH$_2$CH$_2$CH$_2$CH$_3$ | —F | —I$^-$ |

TABLE 4-continued

Products

Formula (II) ($R_4$, $R_7$, $R_8$, $R_9$, $R_{10}$, and $R_{11}$ are H)

| Compound | $R_1$ | $R_2$ | $R_3$ | $R_6$ | $X^-$ |
|---|---|---|---|---|---|
| 5 | —$CH_3$ | —$CH_3$ | —$CH_3$ | —Cl | —$I^-$ |
| 6 | —$CH_2CH_3$ | —$CH_2CH_3$ | —$CH_2CH_3$ | —Cl | —$I^-$ |
| 7 | —$CH_2CH_2CH_3$ | —$CH_2CH_2CH_3$ | —$CH_2CH_2CH_3$ | —Cl | —$I^-$ |
| 8 | —$CH_2CH_2CH_2CH_3$ | —$CH_2CH_2CH_2CH_3$ | —$CH_2CH_2CH_2CH_3$ | —Cl | —$I^-$ |
| 9 | —$CH_3$ | —$CH_3$ | —$CH_3$ | —Br | —$I^-$ |
| 10 | —$CH_2CH_3$ | —$CH_2CH_3$ | —$CH_2CH_3$ | —Br | —$I^-$ |
| 11 | —$CH_2CH_2CH_3$ | —$CH_2CH_2CH_3$ | —$CH_2CH_2CH_3$ | —Br | —$I^-$ |
| 12 | —$CH_2CH_2CH_2CH_3$ | —$CH_2CH_2CH_2CH_3$ | —$CH_2CH_2CH_2CH_3$ | —Br | —$I^-$ |
| 13 | —$CH_3$ | —$CH_3$ | —$CH_3$ | —I | —$I^-$ |
| 14 | —$CH_2CH_3$ | —$CH_2CH_3$ | —$CH_2CH_3$ | —I | —$I^-$ |
| 15 | —$CH_2CH_2CH_3$ | —$CH_2CH_2CH_3$ | —$CH_2CH_2CH_3$ | —I | —$I^-$ |
| 16 | —$CH_2CH_2CH_2CH_3$ | —$CH_2CH_2CH_2CH_3$ | —$CH_2CH_2CH_2CH_3$ | —I | —$I^-$ |

This disclosure relates to specific compounds of formula (II) as shown in Table 5 and the crystalline forms of those compounds disclosed herein.

TABLE 5

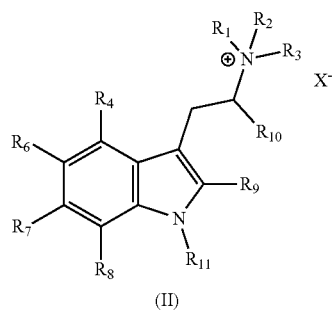

(II)

| Compound | Structural Formula |
|---|---|
| 5-fluoro-N,N,N-trimethyltryptammonium (5-F-TMT) iodide | 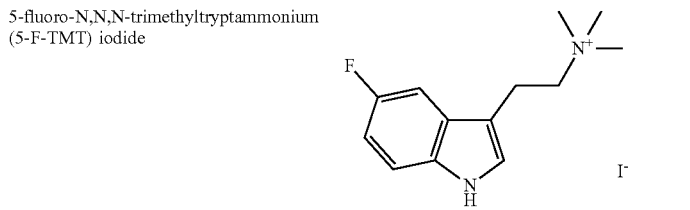 |
| 5-fluoro-N,N,N-triethyltryptammonium (5-F-TET) iodide | 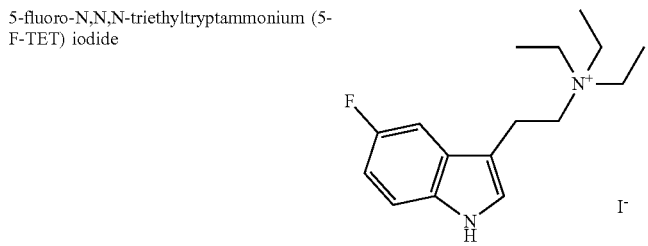 |

TABLE 5-continued (II)

| Compound | Structural Formula |
| --- | --- |
| 5-fluoro-N,N,N-tri-n-propyltryptammonium (5-F-TPT) iodide | |
| 5-chloro-N,N,N-trimethyltrptammonium (5-Cl-TMT) iodide | |
| 5-chloro-N,N,N-triethyltryptammonium (5-Cl-TET) iodide | |
| 5-bromo-N,N,N-triethyltryptammonium (5-Br-TET) iodide | |
| 5-bromo-N,N,N-tri-n-propyltryptammonium (5-Br-TPT) iodide | |

TABLE 5-continued

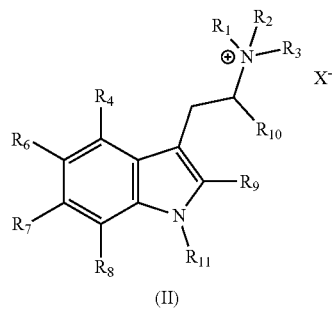

(II)

| Compound | Structural Formula |
| --- | --- |
| 5-bromo-N,N,N-tri-n-propyltryptammonium (5-Br-TPT) iodide acetonitrile solvate | |

Methods of Treatment and Therapeutic Uses

In one embodiment, the compounds of formula (I) or formula (II), according to the disclosure, crystalline forms thereof, and the methods and the compositions (e.g., pharmaceutical compositions) of the disclosure are used to regulate the activity of a neurotransmitter receptor by administering a therapeutically effective dose of compounds of formula (I) or formula (II) according to the disclosure. In another embodiment, the compounds of formula (I) or formula (II), according to the disclosure, and the methods and the compositions (e.g., pharmaceutical compositions) of the disclosure are used to treat inflammation and/or pain by administering a therapeutically effective dose of compounds of formula (I) or formula (II) according to the disclosure.

Methods of the disclosure administer a therapeutically effective amount of compounds of formula (I) or formula (II) to prevent or treat a disease or condition, such as those discussed below. Compounds of formula (I) or formula (II) may be administered neat or as a pharmaceutical composition comprising compounds of formula (I) or formula (II) as discussed below.

Compounds of formula (I) or formula (II), as described herein, may be used to prevent and/or treat a psychological disorder. The disclosure provides a method for preventing and/or treating a psychological disorder by administering to a subject in need thereof a therapeutically effective amount of compounds of formula (I) or formula (II), including the exemplary embodiments discussed herein. The psychological disorder may be chosen from depression, psychotic disorder, schizophrenia, schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

Compounds of formula (I) or formula (II) according to the disclosure may be used to prevent and/or treat a brain disorder. The disclosure provides a method for preventing and/or treating a brain disorder by administering to a subject in need thereof a therapeutically effective amount of compounds of formula (I) or formula (II) including, but not limited to, the exemplary embodiments discussed herein. The brain disorder may be chosen from Huntington's disease, Alzheimer's disease, dementia, and Parkinson's disease.

Compounds of formula (I) or formula (II) according to the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of compounds of formula (I) or formula (II), including, but not limited to, the exemplary embodiments discussed herein.

Compounds of formula (I) or formula (II) according to the disclosure may be used to prevent and/or treat inflammation and/or pain, such as, for example, inflammation and/or pain associated with inflammatory skeletal or muscular diseases or conditions. Accordingly, the disclosure relates to a method for preventing and/or treating inflammation and/or pain by administering to a subject in need thereof a therapeutically effective amount of compounds of formula (I) or formula (II), including, but not limited to, the exemplary embodiments discussed herein. Generally speaking, treatable "pain" includes nociceptive, neuropathic, and mix-type. A method of the disclosure may reduce or alleviate the symptoms associated with inflammation, including, but not limited to, treating localized manifestation of inflammation characterized by acute or chronic swelling, pain, redness, increased temperature, or loss of function in some cases. A method of the disclosure may reduce or alleviate the symptoms of pain regardless of the cause of the pain, including, but not limited to, reducing pain of varying severity, e.g., mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include, but are not limited to, musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Compounds of formula (I) or formula (II) according to the disclosure may be used to modulate activity of a mitogen activating protein (MAP), comprising administering a composition of the disclosure. In one embodiment, the mitogen activating protein (MAP) comprises a MAP kinase (MAPk). MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, Janus Kinase 1 (JAK1), and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-α. In the central nervous system, p38-alpha regulates neuronal death and neurite degeneration, and it is a common target of Alzheimer's disease therapies. JAK1 influences cytokine signaling, including IL-2, IL-4, IFN-alpha/beta, IFN-γ, and IL-10, and it is implicated in brain aging. JNK3 is neuronal specific protein isoform of the JNKs. It is involved with the regulation of apoptosis. JNK3 also plays a role in modulating the response of cytokines, growth factors, and oxidative stress.

As used herein, the term "modulating activity of a mitogen activating protein" refers to changing, manipulating, and/or adjusting the activity of a mitogen activating protein. In one embodiment, modulating the activity of a MAP, such as a MAPK, can influence neural health, neurogenesis, neural growth and differentiation, and neurodegenerative diseases.

Compounds of formula (I) or formula (II) according to the disclosure may be used to modulate neurogenesis, comprising administering a composition of the disclosure. As used herein, the term "modulating neurite outgrowth" refers to changing, manipulating, and/or adjusting the growth and development of neural projections, or "neurites." In one embodiment, neurogenesis comprises modulating the growth of new neurites, the number of neurites per neuron, and/or neurite length. In one embodiment, modulating neurite outgrowth comprises increasing and/or enhancing the rate and/or length at which neurites develop.

Compounds of formula (I) or formula (II) according to the disclosure may be used to modulate neurite outgrowth, comprising administering a composition of the disclosure. As used herein, the term "modulating neurogenesis" refers to changing, manipulating, and/or adjusting the growth and development of neural tissue. In one embodiment, neurogenesis comprises adult neurogenesis, in which new neural stem cells are generated from neural stem cells in an adult animal. In one embodiment, modulating neurogenesis comprises increasing and/or enhancing the rate at which new neural tissue is developed.

The disclosure also relates to methods of preventing or treating sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

The disclosure also relates to methods of preventing or treating women's health disorders including, but not limited to, menstrual cramping, dysmenorrhea, post-hysterectomic pain, vaginal or vulvar vestibule mucosa disorder, vaginal atrophy, or vulvar vestibulitis.

The disclosure also relates to a method of generating a dialkyltryptamine compound in situ in a patient, the method comprising administering at least one quaternary tryptamine compound selected from formula (I) or (II) to the patient. The disclosure also relates to methods of generating a dialkyltryptamine compound comprising contacting at least one quaternary tryptamine compound selected from formula (I) or (II) with an enzyme in vitro or in vivo, such as an enzyme capable of nitrogen dealkylation (e.g., cytochrome P450 enzymes (CYPs)). The disclosure further relates to methods of generating a dialkyltryptamine compound in situ in a patient comprising contacting at least one quaternary tryptamine compound selected from formula (I) or (II) with an enzyme in the patient capable of nitrogen dealkylation (e.g., cytochrome P450 enzymes (CYPs)).

Compositions

The disclosure also relates to compositions comprising an effective amount of a compound of formula (I) or formula (II), including 5-F-TMT iodide, 5-F-TET iodide, 5-F-TPT iodide, 5-Cl-TMT iodide, 5-Cl-TET iodide, 5-Br-TET iodide, 5-Br-TPT iodide, 5-Br-TPT iodide acetonitrile solvate, their crystalline forms, and crystalline 5-Br-TMT iodide, according to the disclosure (quaternary tryptamine compounds of the disclosure), including its exemplary embodiments discussed above, and an excipient (e.g., a pharmaceutically-acceptable excipient). In another embodiment, the disclosure also relates to pharmaceutical compositions comprising a therapeutically effective amount of a quaternary tryptamine compounds of the disclosure, including its exemplary embodiments discussed above, and a pharmaceutically acceptable excipient (also known as a pharmaceutically acceptable carrier). As discussed above, a quaternary tryptamine compound according to the disclosure may be, for example, therapeutically useful to prevent and/or treat the psychological disorders, brain disorders, pain, and inflammation as well as the other disorders described herein.

A composition or a pharmaceutical composition of the disclosure may be in any form which contains a quaternary tryptamine compound of the disclosure. The composition may be, for example, a tablet, capsule, liquid suspension, injectable, topical, or transdermal. The compositions generally contain, for example, about 1% to about 99% by weight of a quaternary tryptamine compound of the disclosure and, for example, 99% to 1% by weight of at least one suitable pharmaceutically acceptable excipient. In one embodiment, the composition may be between about 5% and about 75% by weight of a quaternary tryptamine compound of the disclosure, with the rest being at least one suitable pharmaceutically acceptable excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, a quaternary tryptamine compound of the disclosure may be used as the "first purified psilocybin derivative" in the compositions described in US 2018/0221396 A1 and US 2019/0142851 A1. Accordingly, this disclosure provides a composition comprising: a first component comprising at least one quaternary tryptamine compound of the disclosure; at least one second component selected from (a) a serotonergic drug, (b) a purified psilocybin derivative, (c) a purified cannabinoid and (d) a purified terpene; and at least one pharmaceutically-acceptable excipient or at least one other adjuvant. Such a composition may be a pharmaceutical composition wherein the components are present individually in therapeutically effective amounts or by combination in a therapeutically effective amount to treat a disease, disorder, or condition as described herein. When used in such compositions as a first component comprising one or more of the quaternary tryptamine compounds of the disclosure with a second component selected from (a) a serotonergic drug, (b) a purified psilocybin derivative, (c) one or two purified cannabinoids, and (d) a purified terpene, the compositions represent particular embodiments of the disclosure. Compositions having a combination of a quaternary tryptamine compound of the disclosure as a first component with a second component selected from (e) an adrenergic drug, (f) a dopaminergic drug, (g) a monoamine oxidase inhibitor, (h) a purified erinacine, and (i) a purified hericenone represent additional particular embodiments of the disclosure represented by the compositions having the quaternary tryptamine compounds of the disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated here by reference. Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed exemplary embodiments. Exemplary cannabinoids include but are not limited to the cannabinoids described in paragraphs [0111]-[0159] of US 2018/0221396 A1 and [0112]-[0160] US 2019/0142851 A1 as well as the disclosed exemplary embodiments. Exemplary terpenes include but are not limited to the terpenes described in paragraphs [0160]-[0238] of US 2018/0221396 A1 and [0161]-[0300] US 2019/0142851 A1 as well as the disclosed exemplary embodiments.

A pharmaceutical formulation of the disclosure may comprise, consist essentially of, or consist of (a) at least one quaternary tryptamine compound of the disclosure and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and (c) a pharmaceutically acceptable excipient. In some embodiments, the quaternary tryptamine compound(s) of the disclosure and the second active compound(s) are each present in a therapeutically effective amount using a purposefully engineered and unnaturally occurring molar ratios. Exemplary molar ratios of the quaternary tryptamine compound of the disclosure to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing a quaternary tryptamine compound of the disclosure and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. The disclosures of US 2018/0221396 A1 and US 2019/0142851 A1 are incorporated herein by reference. According to this disclosure composition containing a quaternary tryptamine compound of the disclosure as discussed above may be used in place of a "purified psilocybin derivative" in the compositions described in US 2018/0221396 A1 and US 2019/0142851 A1. Accordingly, the disclosure provides a pharmaceutical formulation comprising as (a) at least one quaternary tryptamine compound of the disclosure and at least one second component selected from (a) a purified psilocybin derivative, (b) one or two purified cannabinoids or (c) a purified terpene; and at least one pharmaceutically-acceptable excipient or at least one other adjuvant, as described herein. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated here by reference. Some exemplary serotonergic drugs include SSRIs and SNRIs. Some examples of specific serotonergic drugs include the following molecules, including any salts, solvates, or polymorphs thereof: 6-Allyl-N,N-diethyl-NL, N,N-

Dibutyl-T, N,N-Diethyl-T, N,N-Diisopropyl-T, 5-Methyoxy-alpha-methyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N, N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-N L, N,N-Tetramethylene-T, Tryptamine, and 7-Methoxy-1-methyl-1,2,3,4-tetrahydro-C, alpha,N-Dimethyl-5-methoxy-T. For additional information regarding these compounds see Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In an exemplary embodiment, the serotonergic drug is 3,4-methylenedioxymethamphetamine.

Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed exemplary embodiments, incorporated here by reference. In one embodiment, the compositions disclosed herein comprise one or more purified psilocybin derivatives chosen from: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl]dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine.

Exemplary cannabinoids include but are not limited to the cannabinoids described in paragraphs [0111]-[0159] of US 2018/0221396 A1 and [0112]-[0160] US 2019/0142851 A1 as well as the disclosed exemplary embodiments, incorporated here by reference. Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBDV), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), Cannabitriolvarin (CBTV), 10-Ethoxy-9-hydroxy-delta-6a-tetrahydrocannabinol, Cannbicitran (CBT), Cannabiripsol (CBR), 8,9-Dihydroxy-delta-6a-tetrahydrocannabinol, Delta-8-tetrahydrocannabinol (A8-THC), Delta-8-tetrahydrocannabinolic acid (A8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-metha-no-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed exemplary embodiments, incorporated here by reference. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant. In one embodiment, an adrenergic drug is a norepinephrine transporter inhibitor. In one embodiment, an adrenergic drug is a vesicular monoamine transporter inhibitor. In one embodiment, an adrenergic drug is chosen from adrenaline, agmatine, amoxapine, aptazapine, atomoxetine, bupropion, clonidine, doxepin, duloxetine, esmirtazpine, mianserin, ketanserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor. In one embodiment, a dopaminergic drug is a vesicular monoamine transporter inhibitor. In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

As used herein, the term "monoamine oxidase inhibitor" (MAOI) refers to a compound that blocks the actions of monoamine oxidase enzymes. In on embodiment, a MAOI inhibits the activity of one or both monoamine oxidase A and monoamine oxidase B. In one embodiment a MAOI is a reversible inhibitors of monoamine oxidase A. In one embodiment a MAOI is a drug chosen from isocarboxazid, phenelzine, or tranylcypromine.

In one embodiment, the compositions and methods disclosed herein include one or more purified erinacine molecules. In one embodiment, the compositions and methods disclosed herein comprise purified erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D. In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine J. In one embodiment, the compositions and methods disclosed herein comprise erinacine K In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S.

In one embodiment, the compositions and methods disclosed herein include one or more purified hericenone molecules. In one embodiment, the compositions and methods disclosed herein comprise purified hericenone A. In one embodiment, the compositions and methods disclosed herein comprise purified hericenone B. In one embodiment, the compositions and methods disclosed herein comprise purified hericenone C. In one embodiment, the compositions and methods disclosed herein comprise purified hericenone D. In one embodiment, the compositions and methods disclosed herein comprise purified hericenone E. In one embodiment, the compositions and methods disclosed herein comprise purified hericenone F. In one embodiment, the compositions and methods disclosed herein comprise purified hericenone G. In one embodiment, the compositions and methods disclosed herein comprise purified hericenone H.

Exemplary compositions of a quaternary tryptamine compound of the disclosure, for example a compound of formula (I) or a compound of formula (II), and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone in exemplary molar ratios are shown in Table 6. A quaternary tryptamine compound of the disclosure may be any one of the exemplary embodiments described above; with the proviso that for a compound of formula (II) when $R_1$, $R_2$, and $R_3$ are methyl and $R_4$, $R_7$, $R_8$, $R_9$, $R_{10}$, and $R_{11}$ are hydrogen, $R_6$ is not Br.

TABLE 6

| Second Compound | Molar ratio of a quaternary tryptamine compound of the disclosure:second compound | Molar ratio of a quaternary tryptamine compound of the disclosure:second compound | Molar ratio of a quaternary tryptamine compound of the disclosure:second compound |
| --- | --- | --- | --- |
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

Exemplary pharmaceutical compositions of a quaternary tryptamine compound of the disclosure, for example a compound of formula (I) or a compound of formula (II), and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and an excipient with exemplary molar ratios of a quaternary tryptamine compound of the disclosure to the second compound are shown in Table 7. A quaternary tryptamine compound of the disclosure may be any one of the exemplary embodiments described above; with the proviso that for a compound of formula (II) when $R_1$, $R_2$, and $R_3$ are methyl and $R_4$, $R_7$, $R_8$, $R_9$, $R_{10}$, and $R_{11}$ are hydrogen, $R_6$ is not Br.

TABLE 7

| Second Compound | Molar ratio of a quaternary tryptamine compound of the disclosure:second compound | Molar ratio of a quaternary tryptamine compound of the disclosure:second compound | Molar ratio of a quaternary tryptamine compound of the disclosure:second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

An "effective amount" or a "therapeutically effective amount" of a quaternary tryptamine compound of the disclosure is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. A quaternary tryptamine compound of the disclosure and pharmaceutical compositions containing it may be used in combination with other agents that are generally administered to a patient being treated for psychological and other disorders discussed above. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Exemplary carriers include those that do not substantially alter the structure or activity of the quaternary tryptamine compounds of the disclosure or produce undesirable biological effects or otherwise interact in a deleterious manner with any other component(s) of the pharmaceutical composition.

The pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, a quaternary tryptamine compound of the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. In some embodiments, the excipient is not water. In some embodiments, the excipient is not a solvent (e.g., EtOH, diethyl ether, ethyl acetate, or hydrocarbon-based solvents (e.g., hexanes). In some embodiments, the dosage form is substantially free of water and/or solvents, for example less than about 5% water by mass, less than 2% water by mass, less than 1% water by mass, less than 0.5% water by mass, or less than 0.1% water by mass.

Excipients or pharmaceutically acceptable adjuvants known in the pharmaceutical formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of a quaternary tryptamine compound of the disclosure in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

The preparation of compounds of formula (II), including crystalline 5-F-TMT iodide, crystalline 5-F-TET iodide, crystalline 5-F-TPT iodide, crystalline 5-Cl-TMT iodide, crystalline 5-Cl-TET iodide, crystalline 5-Br-TET iodide, crystalline 5-Br-TPT iodide, and crystalline 5-Br-TPT iodide acetonitrile solvate are described below.

Example 1: Synthesis and Crystallization of 5-fluoro-N,N,N-trimethyltryptammonium (5-F-TMT) iodide 146 mg of 5-fluorotryptamine was dissolved in 10 mL of isopropanol, and 261 mg of sodium carbonate and 0.4 mL of iodomethane were then added. The mixture was refluxed under nitrogen for 24 hrs. Solvent was removed in vacuo to yield an orange powder. The powder was washed with water and isolated via vacuum filtration. The powder was washed in diethyl ether and dried under vacuum. 130 mg of light-yellow powder was collected (45% yield). Crystal suitable for X-ray diffraction studies were grown from the slow evaporation of an acetone solution.

$^1$H NMR (400 MHz, CDCl$_3$): δ 7.48 (q, J=4.4 Hz, 1H, ArH), 7.39-7.36 (m, 2H, ArH), 7.09-7.03 (m, 1H, ArH), 3.65-3.61 (m, 2H, CH$_2$), 3.32-3.28 (m, 2H, CH$_2$), 3.23 (s, 9H, CH$_3$).

Single crystal data, data collection and structure refinement details of crystalline 5-F-TMT iodide are summarized in Table 8.

Figure 2:
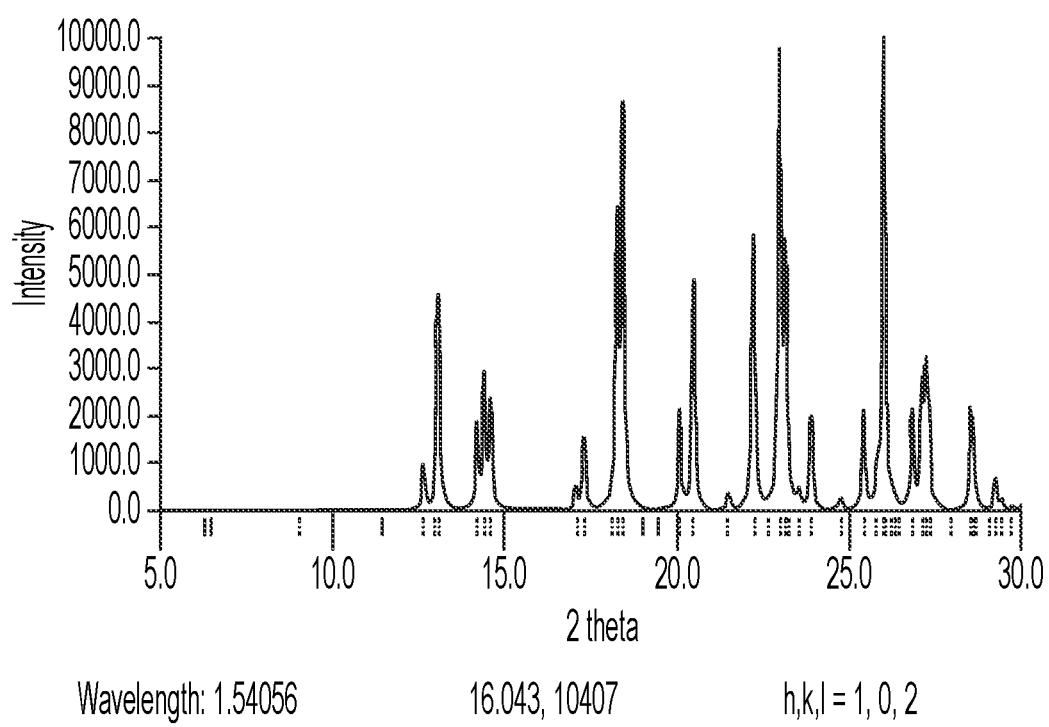
FIG. 2 shows a simulated x-ray powder diffraction (XRPD) of crystalline 5-F-TMT iodide from its single crystal data.

Crystalline 5-F-TMT iodide may be characterized by the XRPD peaks at 13.1, 20.5, and 22.2°2θ±0.2°2θ as well as by an XRPD pattern substantially similar to FIG. 2.

TABLE 8

|  | 5-fluoro-N,N,N-trimethyltryptammonium iodide |
| --- | --- |
| Chemical formula | I•$C_{13}H_{18}FN_2$ |
| $M_r$ | 348.19 |
| Crystal system, space group | Orthorhombic, $P2_12_12_1$ |
| Temperature (K) | 297 |
| a, b, c (Å) | 7.7261 (4), 13.6571 (6), 13.9972 (7) |
| V (Å$^3$) | 1476.93 (12) |
| Z | 4 |
| F(000) | 688 |
| $D_x$ (Mg m$^{-3}$) | 1.566 |
| Radiation type | $M_o K_\alpha$ |
| λ (Å) | 0.71073 |
| θ (°) | 2.9-26.0 |
| μ (mm$^{-1}$) | 2.16 |
| Crystal size (mm) | 0.24 × 0.08 × 0.06 |
| PLATE | Colourless |
| Diffractometer | Bruker D8 Venture CMOS |
| Absorption correction | Multi-scan |
|  | SADABS2016/2 (Bruker, 2016/2) was used for absorption correction. wR2(int) was 0.0632 before and 0.0541 after correction. The Ratio of minimum to maximum transmission is 0.8834. The λ/2 correction factor is not present. |
| $T_{min}$, $T_{max}$ | 0.659, 0.745 |
| No. of measured, independent, and observed [I > 2s(I)] reflections | 28378, 2998, 2360 |
| $R_{int}$ | 0.043 |
| $θ_{max}$, $θ_{min}$ (°) | 26.4, 2.9 |
| h, k, l | −9→9, −16→17, −17→17 |
| Refinement | $F^2$ |
| R[$F^2 > 2σ(F^2)$], wR($F^2$), S | 0.028, 0.073, 1.13 |
| w | $1/[σ^2(F_o^2) + (0.0217P)^2 + 1.1374P]$ where P = $(F_o^2 + 2F_c^2)/3$ |
| No. of reflections | 2998 |
| No. of parameters | 161 |
| No. of restraints | 1 |
| H-site location | mixed |
| H-atom treatment | H atoms treated by a mixture of independent and constrained refinement |
| $(Δ/σ)_{max}$ | 0.001 |
| $Δ>_{max}$, $Δ>_{min}$ (e Å$^{-3}$) | 0.56, −0.63 |
| Absolute Structure | Refined as an inversion twin |
| Absolute Structure Parameter | 0.10 (5) |

Data collection: Bruker APEX3; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

The molecular structure of crystalline 5-F-TMT iodide, showing the atom labeling, is shown in FIG. 1.

FIG. 2 is a simulated x-ray powder diffraction (XRPD) of crystalline 5-F-TMT iodide from its single crystal data.

Example 2: Synthesis and Crystallization of 5-fluoro-N,N,N-triethyltryptammonium (5-F-TET) iodide 143 mg of 5-Fluoro Tryptamine was dissolved in 10 mL of isopropanol, 256 mg of $Na_2CO_3$ and 0.5 mL of Ethyl Iodide were then added. The mixture was refluxed under nitrogen for 24 hrs. The solvent was stripped off on a rotovap, orange powder was obtained. The powder was washed in DI water then filtered under vacuum. The powder was washed again in ether then placed under vacuum for 2 days. 180 mg of light-yellow powder was collected.

The percent yield was calculated as 58.08%.

$^1$H NMR (400 MHz, CDCl$_3$): δ 7.49 (q, J=4.5 Hz, 1H, ArH), 7.37-7.33 (m, 2H, ArH), 7.09-7.04 (m, 1H, ArH), 3.44-3.37 (m, 8H, CH$_2$), 3.18-3.14 (m, 2H, CH$_2$), 1.33 (t, J=7.2 Hz, 9H, CH$_3$).

Single crystal data, data collection and structure refinement details of crystalline 5-F-TET iodide are summarized in Table 9.

Data collection: Bruker APEX3; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

Figure 3:
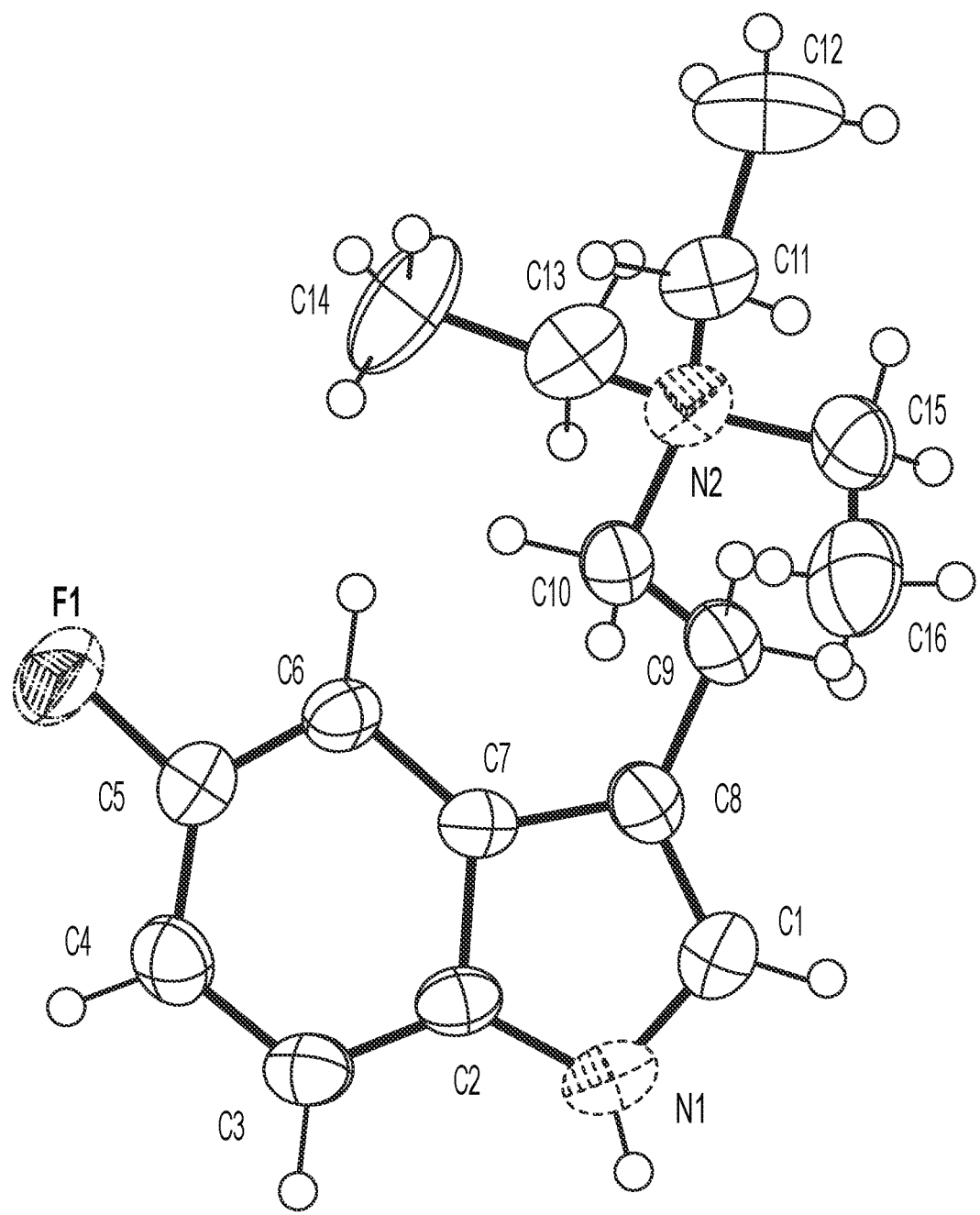
FIG. 3 shows the molecular structure of crystalline 5-fluoro-N,N,N-triethyltryptammonium (5-F-TET) iodide, showing the atom labeling.

The molecular structure of crystalline 5-F-TET iodide, showing the atom labeling, is shown in FIG. 3.

TABLE 9

| | 5-fluoro-N,N,N-triethyltryptammonium iodide |
|---|---|
| Chemical formula | I·C$_{16}$H$_{24}$FN$_2$ |
| M$_r$ | 390.27 |
| Crystal system, space group | Orthorhombic, P2$_1$2$_1$2$_1$ |
| Temperature (K) | 297 |
| a, b, c (Å) | 8.5885 (4), 13.6650 (6), 14.6306 (7) |
| V (Å$^3$) | 1717.07 (14) |
| Z | 4 |
| F(000) | 784 |
| D$_x$ (Mg m$^{-3}$) | 1.510 |
| Radiation type | M$_o$ K$_\alpha$ |
| λ (Å) | 0.71073 |
| θ (°) | 2.8-26.4 |
| μ (mm$^{-1}$) | 1.87 |
| Crystal size (mm) | 0.22 × 0.18 × 0.14 |
| BLOCK | Colourless |
| Diffractometer | Bruker D8 Venture CMOS |
| Absorption correction | Multi-scan |
| | SADABS2016/2 (Bruker, 2016/2) was used for absorption correction. wR2(int) was 0.0600 before and 0.0475 after correction. The Ratio of minimum to maximum transmission is 0.9276. The λ/2 correction factor is not present. |
| T$_{min}$, T$_{max}$ | 0.691, 0.745 |
| No. of measured, independent, and observed [I > 2s(I)] reflections | 53582, 3468, 3410 |
| R$_{int}$ | 0.023 |
| θ$_{max}$, θ$_{min}$ (°) | 26.4, 3.2 |
| h, k, l | −10→10, −16→17, −18→18 |
| Refinement | F$^2$ |
| R[F$^2$ > 2σ(F$^2$)], wR(F$^2$), S | 0.015, 0.037, 1.09 |
| w | 1/[σ$^2$(F$_o^2$) + (0.0147P)$^2$ + 0.4873P] where P = (F$_o^2$ + 2F$_c^2$)/3 |
| No. of reflections | 3468 |
| No. of parameters | 188 |
| No. of restraints | 0 |
| H-site location | mixed |
| H-atom treatment | H atoms treated by a mixture of independent and constrained refinement |
| (Δ/σ)$_{max}$ | 0.002 |
| Δ$\rangle_{max}$, Δ$\rangle_{min}$ (e Å$^{-3}$) | 0.27, −0.29 |
| Absolute Structure | Flack x determined using 1445 quotients |
| Absolute Structure Parameter | [(I+) − (I−)]/[(I+) + (I−)] (Parsons, Flack and Wagner, Acta Cryst. B69 (2013) 249-259). |
| Absolute Structure Parameter | −0.014 (4) |

Figure 4:
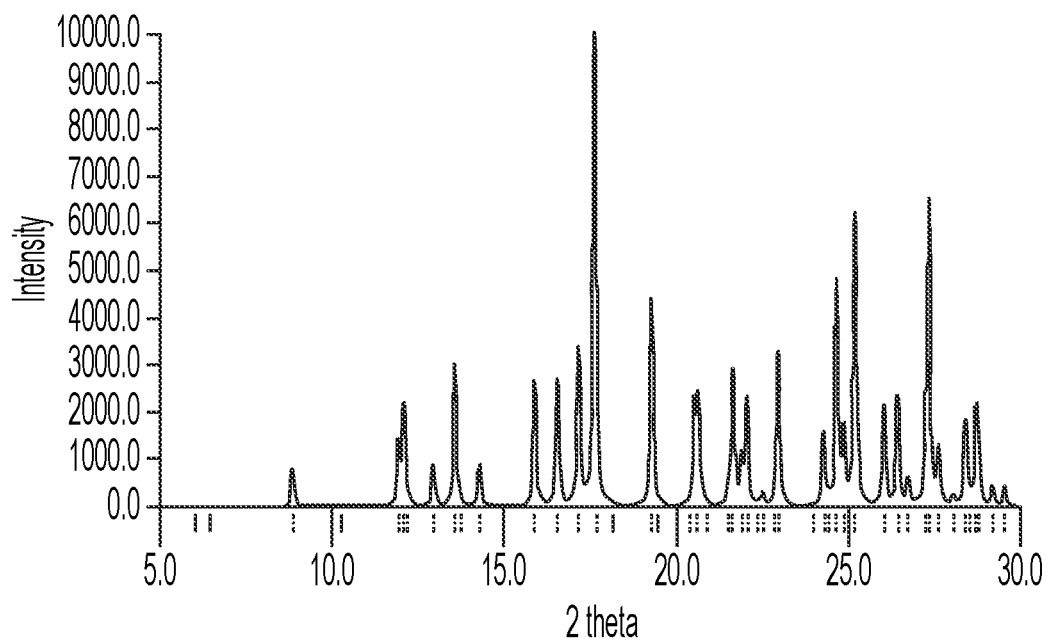
FIG. 4 shows a simulated x-ray powder diffraction (XRPD) of crystalline 5-F-TET iodide from its single crystal data.

FIG. 4 is a simulated x-ray powder diffraction (XRPD) of crystalline 5-F-TET iodide from its single crystal data. Crystalline 5-F-TET iodide may be characterized by the XRPD peaks at 13.6, 15.9, and 16.6°2θ±0.2°2θ as well as by an XRPD pattern substantially similar to FIG. 4.

Example 3: Synthesis and Crystallization of 5-fluoro-N,N,N-tri-n-propyltryptammonium (5-F-TPT) iodide 5-F-TPT iodide was synthesized via the same procedure used in Example 1 but substituting propyl iodide for methyl iodide.

Single crystal data, data collection and structure refinement details of crystalline 5-F-TPT iodide are summarized in Table 10.

Data collection: Bruker APEX3; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

Figure 5:
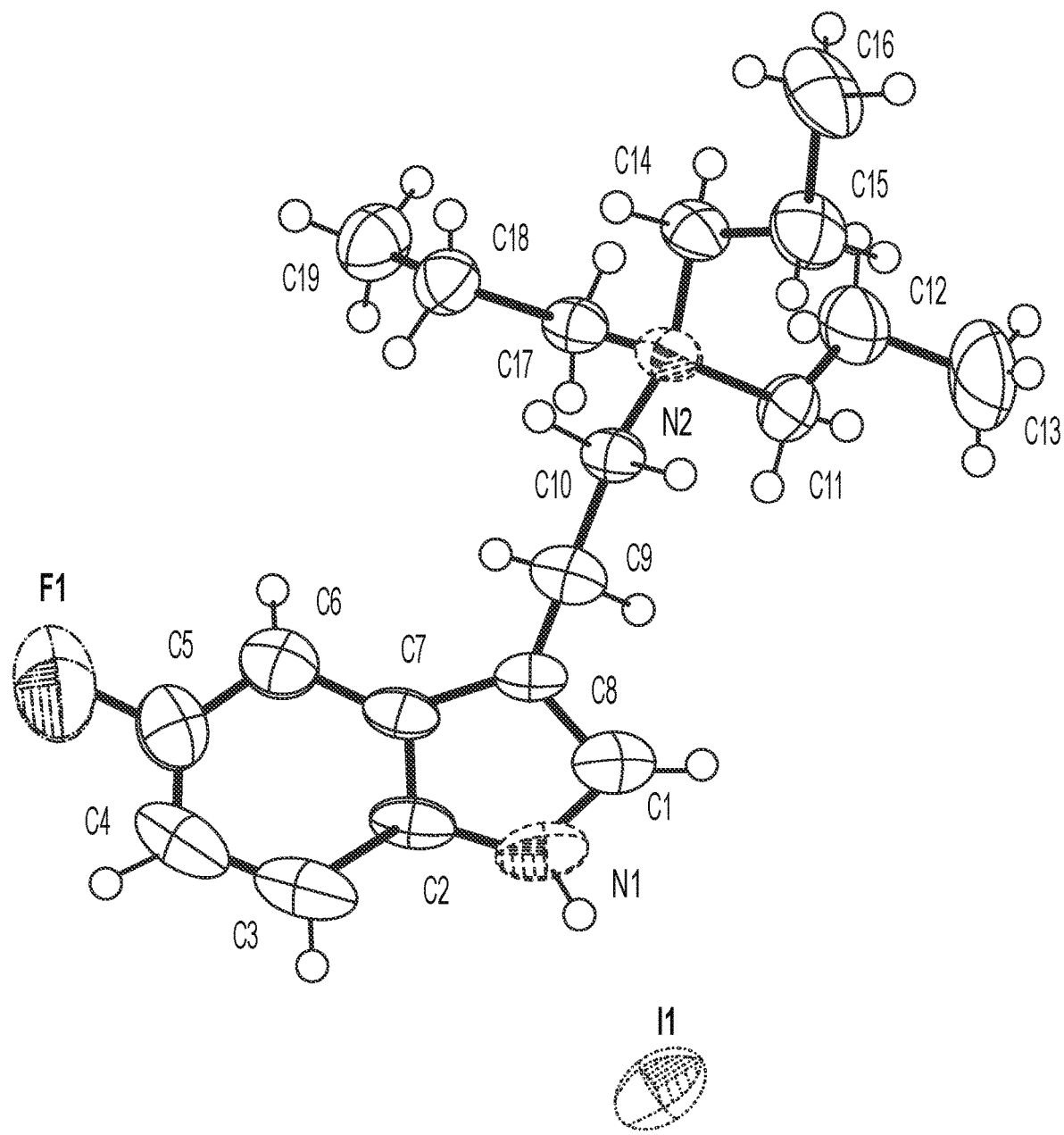
FIG. 5 shows the molecular structure of crystalline 5-fluoro-N,N,N-tri-n-propyltryptammonium (5-F-TPT) iodide, showing the atom labeling.

The molecular structure of crystalline 5-F-TPT iodide, showing the atom labeling, is shown in FIG. 5.

Figure 6:
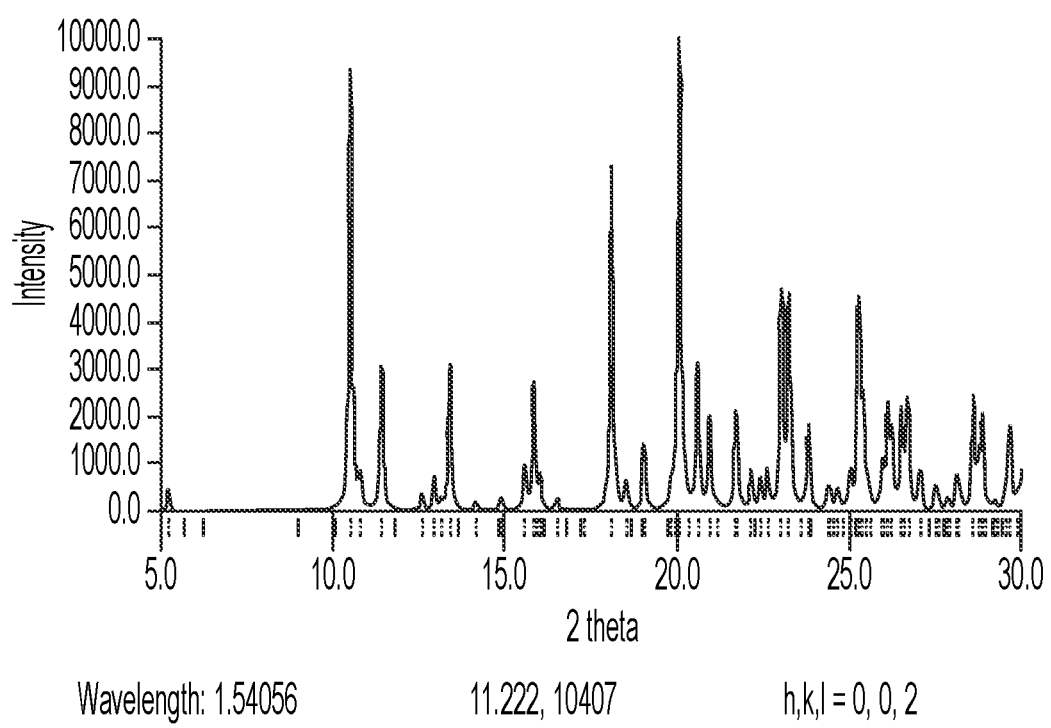
FIG. 6 shows a simulated x-ray powder diffraction (XRPD) of crystalline 5-F-TPT iodide from its single crystal data.

FIG. 6 is a simulated x-ray powder diffraction (XRPD) of crystalline 5-F-TPT iodide from its single crystal data. Crystalline 5-F-TPT iodide may be characterized by the XRPD peaks at 10.6, 13.4, and 18.1°2θ±0.2°2θ as well as by an XRPD pattern substantially similar to FIG. 6.

TABLE 10

|  | 5-fluoro-N,N,N-tri-n-propyltryptammonium iodide |
| --- | --- |
| Chemical formula | I·C$_{19}$H$_{30}$FN$_2$ |
| M$_r$ | 432.35 |
| Crystal system, space group | Monoclinic, P2$_1$/c |
| Temperature (K) | 297 |
| a, b, c (Å) | 17.8375 (9), 7.4586 (3), 16.4361 (7) |
| β (°) | 110.228 (2) |
| V (Å$^3$) | 2051.84 (16) |
| Z | 4 |
| F(000) | 880 |
| D$_x$ (Mg m$^{-3}$) | 1.400 |
| Radiation type | M$_o$ K$_\alpha$ |
| λ (Å) | 0.71073 |
| θ (°) | 2.9-26.3 |
| μ (mm$^{-1}$) | 1.57 |
| Crystal size (mm) | 0.26 × 0.2 × 0.1 |
| BLOCK | Colourless |
| Diffractometer | Bruker APEX-II CCD |
| Absorption correction | Multi-scan |
|  | SADABS2016/2 (Bruker, 2016/2) was used for absorption correction. wR2(int) was 0.0644 before and 0.0463 after correction. The Ratio of minimum to maximum transmission is 0.8822. The λ/2 correction factor is not present. |
| T$_{min}$, T$_{max}$ | 0.658, 0.745 |
| No. of measured, independent, and observed [I > 2s(I)] reflections | 42496, 4188, 3484 |
| R$_{int}$ | 0.033 |
| θ$_{max}$, θ$_{min}$ (°) | 26.4, 2.9 |
| h, k, l | −22→22, −9→9, −20→20 |
| Refinement | F$^2$ |
| R[F$^2$ > 2σ(F$^2$)], wR(F$^2$), S | 0.038, 0.092, 1.05 |
| w | 1/[σ$^2$(F$_o^2$) + (0.0308P)$^2$ + 2.9959P] where P = (F$_o^2$ + 2F$_c^2$)/3 |
| No. of reflections | 4188 |
| No. of parameters | 215 |
| No. of restraints | 0 |
| H-site location | mixed |
| H-atom treatment | H atoms treated by a mixture of independent and constrained refinement |
| (Δ/σ)$_{max}$ | 0.001 |
| Δ$>_{max}$, Δ$>_{min}$ (e Å$^{-3}$) | 1.12, −0.93 |

Example 4: Synthesis and Crystallization of 5-chloro-N,N,N-trimethyltryptammonium (5-Cl-TMT) iodide 5-Cl-TMT iodide was synthesized via the same procedure used in Example 1. This procedure was repeated using a 5-chloro tryptamine in the presence of excess iodomethane.

Single crystal data, data collection and structure refinement details of crystalline 5-Cl-TMT iodide are summarized in Table 11.

TABLE 11

| | 5-chloro-N,N,N-trimethyltryptammonium iodide |
|---|---|
| Chemical formula | I·$C_{13}H_{18}ClN_2$ |
| $M_r$ | 364.64 |
| Crystal system, space group | Monoclinic, $I2/a$ |
| Temperature (K) | 297 |
| a, b, c (Å) | 13.5105 (15), 14.1488 (8), 15.9096 (9) |
| β (°) | 90.3840 (13) |
| V (Å$^3$) | 3041.2 (4) |
| Z | 8 |
| F(000) | 1440 |
| $D_x$ (Mg m$^{-3}$) | 1.593 |
| Radiation type | $M_o K_\alpha$ |
| λ (Å) | 0.71073 |
| θ (°) | 2.9-26.3 |
| μ (mm$^{-1}$) | 2.26 |
| Crystal size (mm) | 0.24 × 0.15 × 0.15 |
| BLOCK | Colourless |
| Diffractometer | Bruker APEX-II CCD |
| Absorption correction | Multi-scan |
| | SADABS2016/2 (Bruker, 2016/2) was used for absorption correction. wR2(int) was 0.0726 before and 0.0563 after correction. The Ratio of minimum to maximum transmission is 0.8487. The λ/2 correction factor is not present. |
| $T_{min}$, $T_{max}$ | 0.549, 0.647 |
| No. of measured, independent, and observed [I > 2s(I)] reflections | 28265, 3086, 2430 |
| $R_{int}$ | 0.039 |
| $θ_{max}$, $θ_{min}$ (°) | 26.4, 2.9 |
| h, k, l | −16→16, −17→17, −19→19 |
| Refinement | $F^2$ |
| R[$F^2 > 2σ(F^2)$], wR($F^2$), S | 0.036, 0.112, 1.08 |
| w | $1/[σ^2(F_o^2) + (0.0598P)^2 + 5.7979P]$ where P = $(F_o^2 + 2F_c^2)/3$ |
| No. of reflections | 3086 |
| No. of parameters | 161 |
| No. of restraints | 1 |
| H-site location | mixed |
| H-atom treatment | H atoms treated by a mixture of independent and constrained refinement |
| $(Δ/σ)_{max}$ | <0.001 |
| $Δ>_{max}$, $Δ>_{min}$ (e Å$^{-3}$) | 0.84, −0.94 |

Data collection: Bruker APEX3; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

Figure 7:
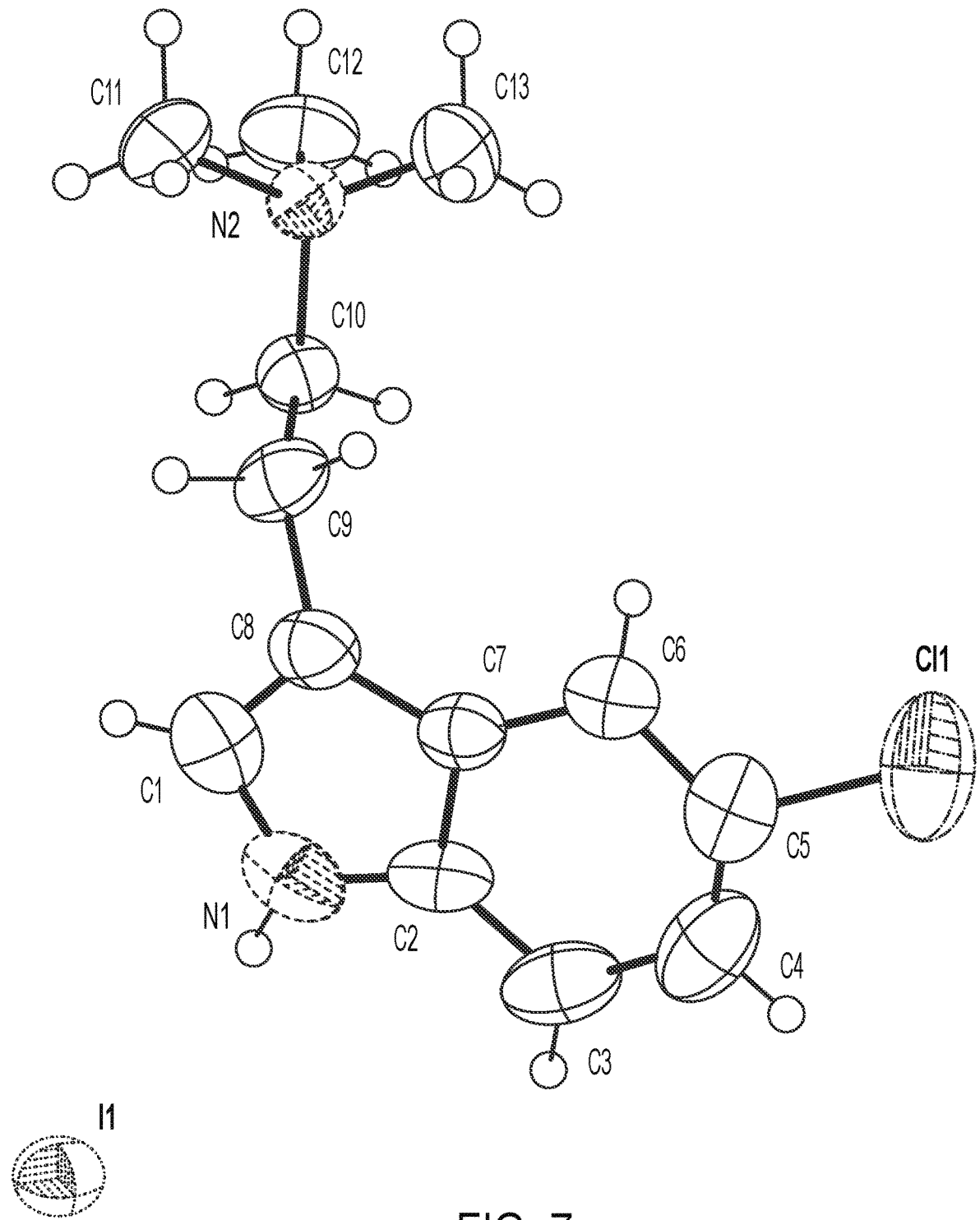
FIG. 7 shows the molecular structure of crystalline 5-chloro-N,N,N-trimethyltryptammonium (5-Cl-TMT) iodide, showing the atom labeling.

The molecular structure of crystalline 5-Cl-TMT iodide, showing the atom labeling, is shown in FIG. 7.

Figure 8:
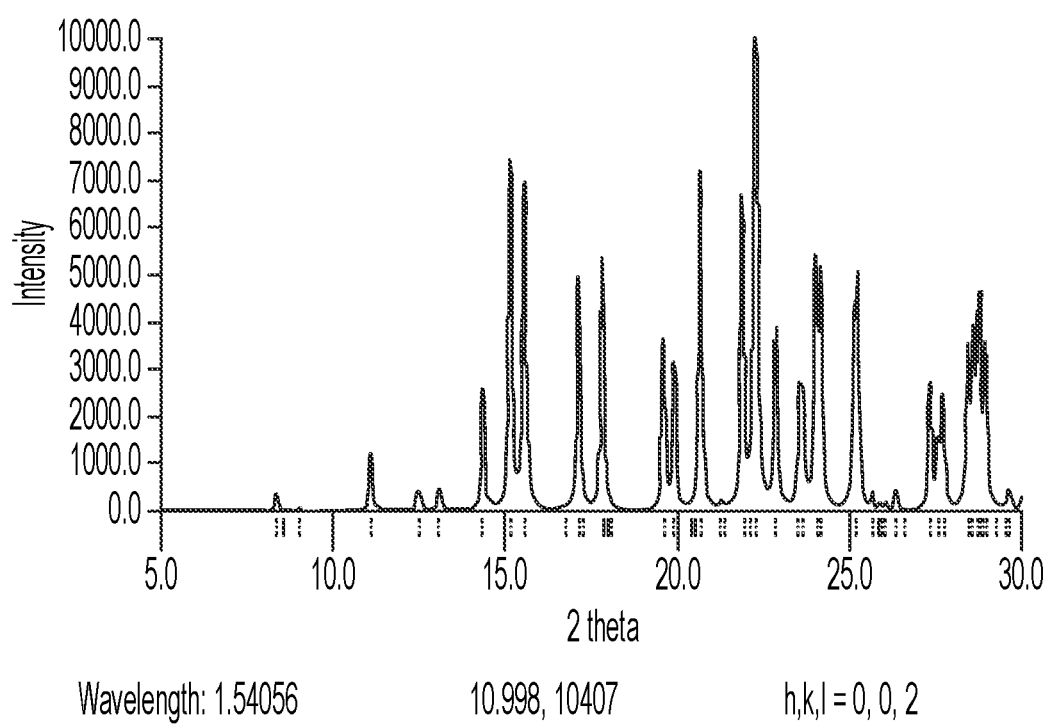
FIG. 8 shows a simulated x-ray powder diffraction (XRPD) of crystalline 5-Cl-TMT iodide from its single crystal data.

FIG. 8 is a simulated x-ray powder diffraction (XRPD) of crystalline 5-Cl-TMT iodide from its single crystal data. Crystalline 5-Cl-TMT iodide may be characterized by the XRPD peaks at 11.1, 14.4, and 20.7° 2θ±0.2° 2θ as well as by an XRPD pattern substantially similar to FIG. 8.

Example 5: Synthesis and Crystallization of 5-chloro-N,N,N-triethyltryptammonium (5-Cl-TET) iodide 106 mg of 5-Chloro Tryptamine was dissolved in 10 mL of isopropanol, 146 mg of $Na_2CO_3$ and 0.3 mL of Ethyl Iodide were then added. The mixture was refluxed under nitrogen for 24 hrs. The solvent was stripped off on a rotovap, orange/yellow powder was obtained. The powder was sonicated in 3 mL of THF for 30 minutes then filtered under vacuum yielding 69 mg of white powder on the frit. This powder was then sonicated in 20 mL of Acetonitrile then filtered under vacuum. Colourless crystals were obtained upon evaporation of the Acetonitrile.

The percent yield was calculated as 77.66%.

Single crystals suitable for X-ray diffraction was obtained from slow evaporation of Acetone solution. The crystals obtained from slow evaporation of Acetonitrile had the same unit cell.

$^1$H NMR (400 MHz, CD$_3$CN): δ 9.53 (s, 1H, NH), 7.60 (d, J=2.0 Hz, 1H, ArH), 7.44 (d, J=8.7 Hz, 1H, ArH), 7.29 (d, J=2.3 Hz, 1H, ArH), 7.15 (dd, J=8.7, 2.0 Hz, 1H, ArH), 3.38-3.30 (m, 8H, CH$_2$), 3.12-3.08 (m, 2H, CH$_2$), 1.29 (tt, J=7.2, 1.8 Hz, 9H, CH$_3$).

Single crystal data, data collection and structure refinement details of crystalline 5-Cl-TET iodide are summarized in Table 12.

TABLE 12

| | 5-chloro-N,N,N-triethyltryptammonium iodide |
|---|---|
| Chemical formula | I·$C_{16}H_{24}ClN_2$ |
| $M_r$ | 406.72 |
| Crystal system, space group | Triclinic, P−1 |
| Temperature (K) | 297 |
| a, b, c (Å) | 12.4760 (13), 12.5317 (12), 13.9873 (16) |
| α (°) | 75.340 (3) |
| β (°) | 68.793 (4) |
| γ (°) | 64.486 (3) |
| V (Å$^3$) | 1827.6 (3) |
| Z | 4 |
| F(000) | 816 |
| $D_x$ (Mg m$^{-3}$) | 1.478 |
| Radiation type | $M_o\,K_\alpha$ |
| λ (Å) | 0.71073 |
| θ (°) | 3.0-26.1 |
| μ (mm$^{-1}$) | 1.89 |
| Crystal size (mm) | 0.2 × 0.2 × 0.03 |
| PLATE | Colourless |
| Diffractometer | Bruker APEX-II CCD |
| Absorption correction | Multi-scan |
| | SADABS2016/2 (Bruker, 2016/2) was used for absorption correction. wR2(int) was 0.0556 before and 0.0447 after correction. The Ratio of minimum to maximum transmission is 0.8958. The λ/2 correction factor is not present. |
| $T_{min}$, $T_{max}$ | 0.668, 0.745 |
| No. of measured, independent, and observed [I > 2s(I)] reflections | 47765, 7503, 6059 |
| $R_{int}$ | 0.035 |
| $\theta_{max}$, $\theta_{min}$ (°) | 26.5, 2.5 |
| h, k, l | −15→15, −15→15, −17→17 |
| Refinement | $F^2$ |
| $R[F^2 > 2\sigma(F^2)]$, $wR(F^2)$, S | 0.037, 0.075, 1.06 |
| w | $1/[\sigma^2(F_o^2) + (0.022P)^2 + 2.0638P]$ where $P = (F_o^2 + 2F_c^2)/3$ |
| No. of reflections | 7503 |
| No. of parameters | 375 |
| No. of restraints | 2 |
| H-site location | mixed |
| H-atom treatment | H atoms treated by a mixture of independent and constrained refinement |
| $(\Delta/\sigma)_{max}$ | <0.001 |
| $\Delta\rangle_{max}$, $\Delta\rangle_{min}$ (e Å$^{-3}$) | 0.95, −0.67 |

Data collection: Bruker APEX3; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

Figure 9:
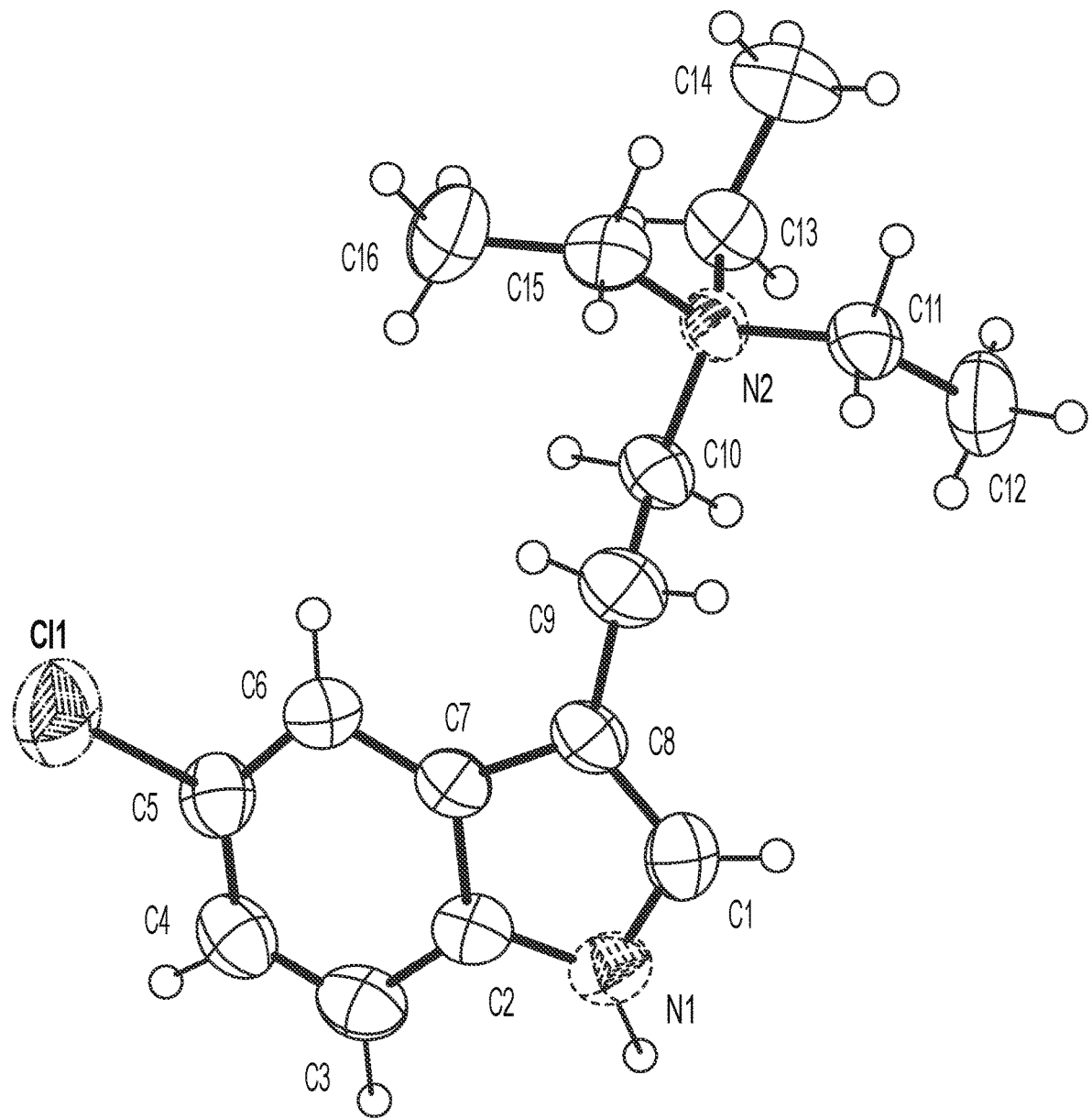
FIG. 9 shows the molecular structure of crystalline 5-chloro-N,N,N-triethyltryptammonium (5-Cl-TET) iodide, showing the atom labeling.

The molecular structure of crystalline 5-Cl-TET iodide, showing the atom labeling, is shown in FIG. 9.

Figure 10:
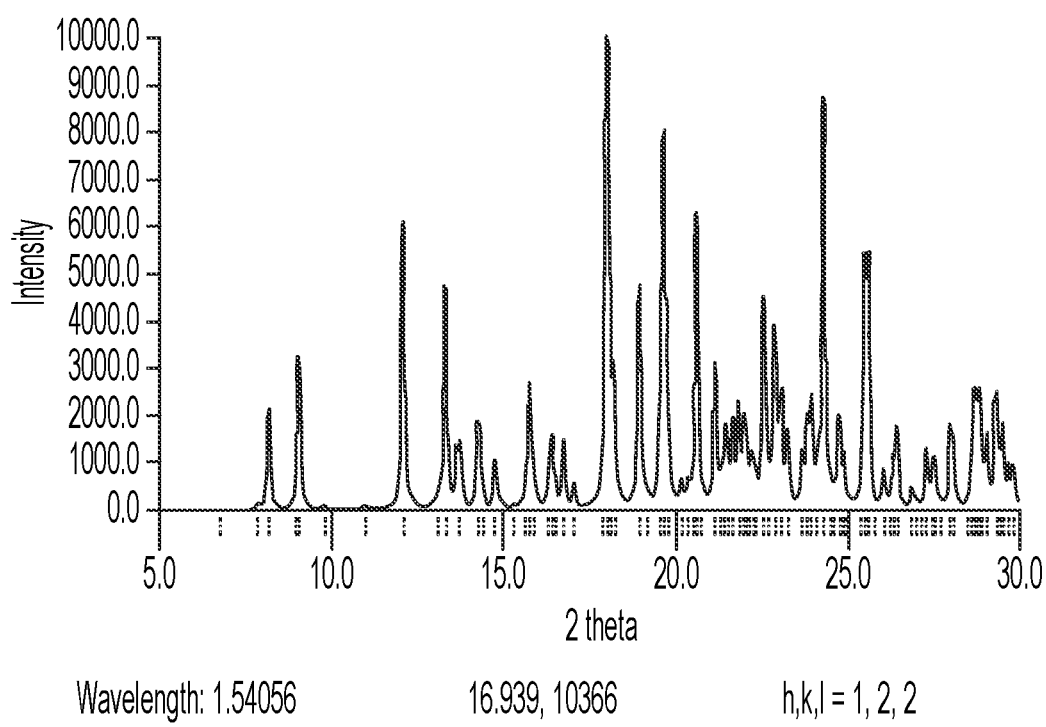
FIG. 10 shows a simulated x-ray powder diffraction (XRPD) of crystalline 5-Cl-TET iodide from its single crystal data.

FIG. 10 is a simulated x-ray powder diffraction (XRPD) of crystalline 5-Cl-TET iodide from its single crystal data. Crystalline 5-Cl-TET iodide may be characterized by the XRPD peaks at 8.2, 9.1, and 12.1° 2θ±0.2° 2θ as well as by an XRPD pattern substantially similar to FIG. 10.

Example 6: Synthesis and Crystallization of 5-bromo-N,N,N-triethyltryptammonium (5-Br-TET) iodide 106 mg of 5-Bromo Tryptamine was dissolved in 10 mL of isopropanol, 141 mg of $Na_2CO_3$ and 0.3 mL of Ethyl Iodide were then added. The mixture was refluxed under nitrogen for 24 hrs. The solvent was stripped off on a rotovap, orange/yellow powder was obtained. The powder was sonicated in 3 mL of THF for 30 minutes then filtered under vacuum yielding 208 mg white powder on the frit. This powder was then sonicated in 20 mL of Acetonitrile then filtered under vacuum. The acetone was then stripped off on the rotovap to obtain a colourless oil product. The oil was recrystallized in acetone resulting in 156 mg of colourless crystals.

The percent yield was calculated as 77.66%.

Single crystals suitable for X-ray diffraction was obtained from slow evaporation of Acetone solution.

$^1$H NMR (400 MHz, $CD_3CN$): δ 9.46 (s, 1H, NH), 7.76 (d, J=1.8 Hz, 1H, ArH), 7.39 (d, J=8.6 Hz, 1H, ArH), 7.29-7.26 (m, 2H, ArH), 3.47-3.29 (m, 8H, $CH_2$), 3.11-3.07 (m, 2H, $CH_2$), 1.28 (tt, J=7.2, 1.8 Hz, 9H, $CH_3$).

Single crystal data, data collection and structure refinement details of crystalline 5-Br-TET iodide are summarized in Table 13.

TABLE 13

| | 5-bromo-N,N,N-triethyltryptammonium iodide |
|---|---|
| Chemical formula | I•C$_{16}$H$_{24}$BrN$_2$ |
| M$_r$ | 451.18 |
| Crystal system, space group | Orthorhombic, P2$_1$2$_1$2$_1$ |
| Temperature (K) | 297 |
| a, b, c (Å) | 9.5921 (4), 13.2918 (7), 14.4411 (7) |
| V (Å$^3$) | 1841.19 (15) |
| Z | 4 |
| F(000) | 888 |
| D$_x$ (Mg m$^{-3}$) | 1.628 |
| Radiation type | M$_o$ K$_\alpha$ |
| λ (Å) | 0.71073 |
| θ (°) | 3.1-26.3 |
| μ (mm$^{-1}$) | 3.90 |
| Crystal size (mm) | 0.24 × 0.21 × 0.1 |
| BLOCK | Colourless |
| Diffractometer | Bruker APEX-II CCD |
| Absorption correction | Multi-scan |
| | SADABS2016/2 (Bruker, 2016/2) was used for absorption correction. wR2(int) was 0.0677 before and 0.0561 after correction. The Ratio of minimum to maximum transmission is 0.8687. The λ/2 correction factor is not present. |
| T$_{min}$, T$_{max}$ | 0.562, 0.647 |
| No. of measured, independent, and observed [I > 2s(I)] reflections | 49433, 3721, 3480 |
| R$_{int}$ | 0.028 |
| θ$_{max}$, θ$_{min}$ (°) | 26.4, 2.6 |
| h, k, l | −11→11, −16→16, −18→18 |
| Refinement | F$^2$ |
| R[F$^2$ > 2σ(F$^2$)], wR(F$^2$), S | 0.022, 0.049, 1.03 |
| w | 1/[σ$^2$(F$_o^2$) + (0.0153P)$^2$ + 1.2042P] where P = (F$_o^2$ + 2F$_c^2$)/3 |
| No. of reflections | 3721 |
| No. of parameters | 188 |
| No. of restraints | 0 |
| H-site location | mixed |
| H-atom treatment | H atoms treated by a mixture of independent and constrained refinement |
| (Δ/σ)$_{max}$ | 0.001 |
| Δ$>_{max}$, Δ$>_{min}$ (e Å$^{-3}$) | 0.56, −0.52 |
| Absolute Structure | Flack x determined using 1456 quotients [(I+) − (I−)]/ |
| Absolute Structure Parameter | [(I+) + (I−)] (Parsons, Flack and Wagner, Acta Cryst. B69 (2013) 249-259). |
| Absolute Structure Parameter | 0.006 (3) |

Data collection: Bruker APEX3; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

Figure 11:
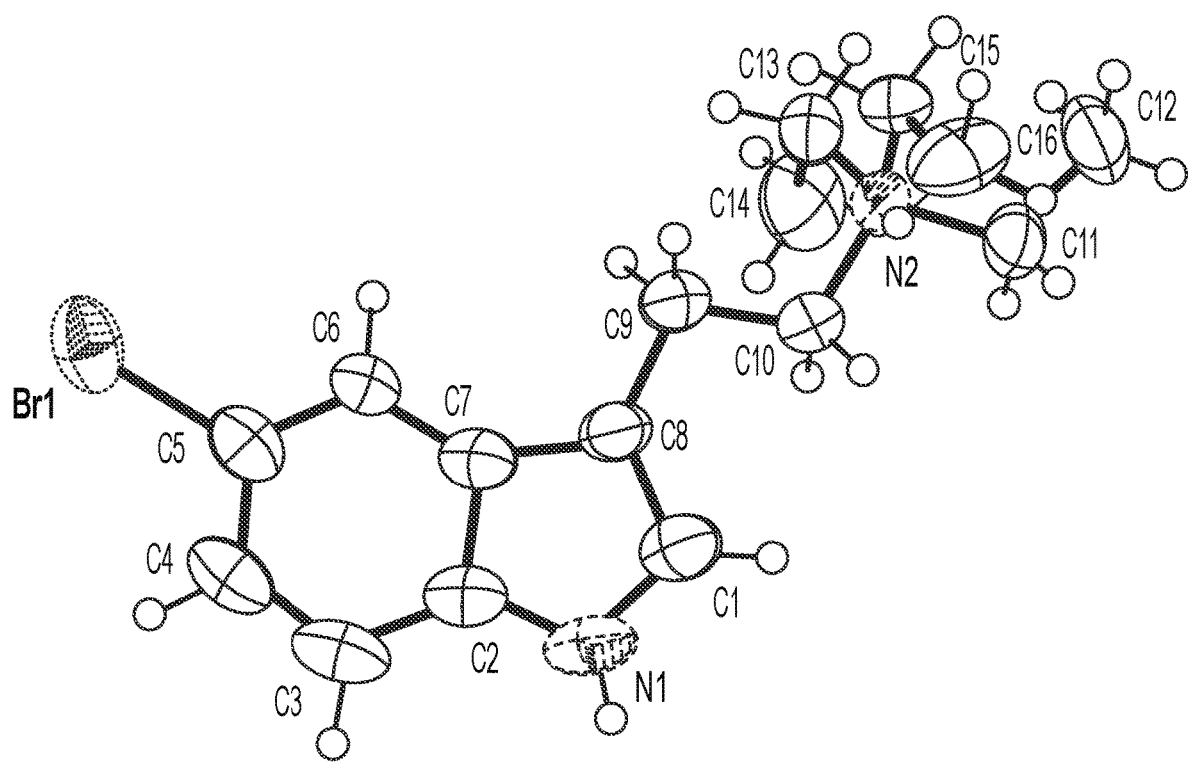
FIG. 11 shows the molecular structure of crystalline 5-bromo-N,N,N-triethyltryptammonium (5-Br-TET) iodide, showing the atom labeling.
Figure 11:

The molecular structure of crystalline 5-Br-TET iodide, showing the atom labeling, is shown in FIG. 11.

Figure 12:
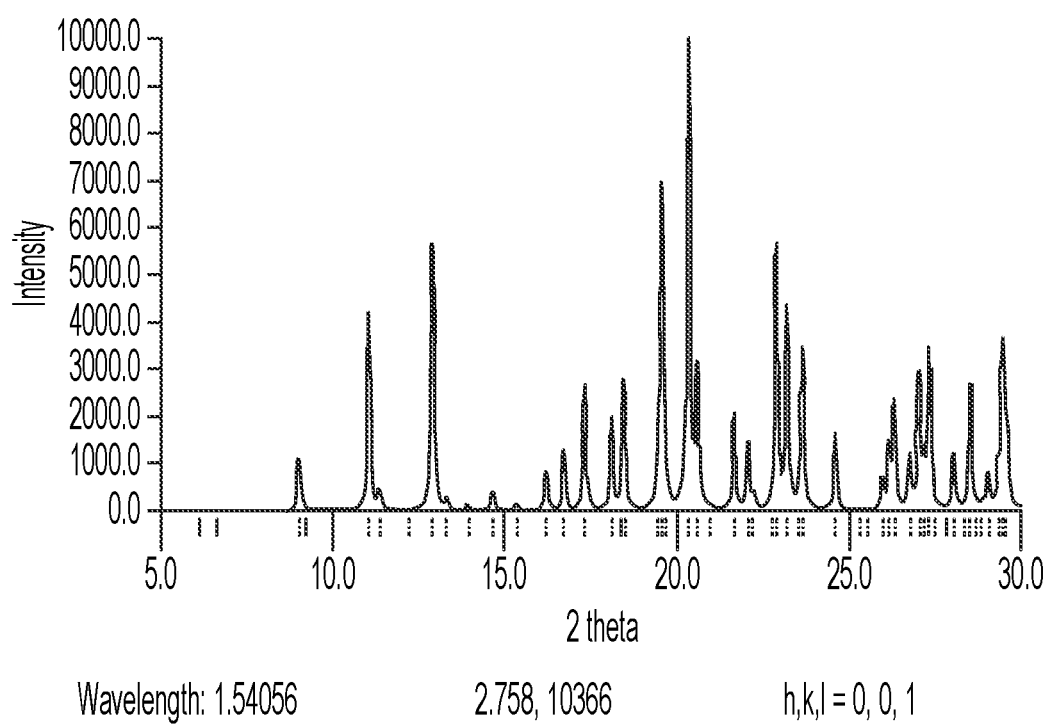
FIG. 12 shows a simulated x-ray powder diffraction (XRPD) of crystalline 5-Br-TET iodide from its single crystal data.

FIG. 12 is a simulated x-ray powder diffraction (XRPD) of crystalline 5-Br-TET iodide from its single crystal data. Crystalline 5-Br-TET iodide may be characterized by the XRPD peaks at 11.1, 12.9, and 20.4° 2θ±0.2° 2θ as well as by an XRPD pattern substantially similar to FIG. 12.

Example 7: Synthesis and Crystallization of 5-bromo-N,N,N-tri-n-propyltryptammonium (5-Br-TPT) iodide 5-Br-TPT iodide was synthesized via the same procedure used in Example 1. This procedure was repeated using a 5-bromo tryptamine in the presence of excess propyl iodide.

Single crystal data, data collection and structure refinement details of crystalline 5-Br-TPT iodide are summarized in Table 14.

TABLE 14

| | 5-bromo-N,N,N-tri-n-propyltryptammonium iodide |
|---|---|
| Chemical formula | I•C$_{19}$H$_{30}$BrN$_2$ |
| M$_r$ | 493.26 |
| Crystal system, space group | Monoclinic, P2$_1$/c |
| Temperature (K) | 297 |
| a, b, c (Å) | 18.2646 (18), 7.6845 (8), 16.2828 (13) |
| β (°) | 110.918 (3) |
| V (Å$^3$) | 2134.7 (4) |
| Z | 4 |
| F(000) | 984 |
| D$_x$ (Mg m$^{-3}$) | 1.535 |

TABLE 14-continued

| | 5-bromo-N,N,N-tri-n-propyltryptammonium iodide |
|---|---|
| Radiation type | $M_o K_\alpha$ |
| $\lambda$ (Å) | 0.71073 |
| $\theta$ (°) | 2.9-26.4 |
| $\mu$ (mm$^{-1}$) | 3.37 |
| Crystal size (mm) | 0.31 × 0.24 × 0.17 |
| BLOCK | Yellow |
| Diffractometer | Bruker APEX-II CCD |
| Absorption correction | Multi-scan |
| | SADABS2016/2 (Bruker, 2016/2) was used for absorption correction. wR2(int) was 0.0856 before and 0.0459 after correction. The Ratio of minimum to maximum transmission is 0.6850. The $\lambda$/2 correction factor is not present. |
| $T_{min}$, $T_{max}$ | 0.511, 0.745 |
| No. of measured, independent, and observed [I > 2s(I)] reflections | 31699, 4330, 3420 |
| $R_{int}$ | 0.035 |
| $\theta_{max}$, $\theta_{min}$ (°) | 26.4, 2.9 |
| h, k, l | $-22 \rightarrow 22$, $-9 \rightarrow 9$, $-20 \rightarrow 19$ |
| Refinement | $F^2$ |
| $R[F^2 > 2\sigma(F^2)]$, $wR(F^2)$, S | 0.035, 0.083, 1.02 |
| w | $1/[\sigma^2(F_o^2) + (0.0254P)^2 + 3.5855P]$ where $P = (F_o^2 + 2F_c^2)/3$ |
| No. of reflections | 4330 |
| No. of parameters | 214 |
| No. of restraints | 1 |
| H-site location | mixed |
| H-atom treatment | H atoms treated by a mixture of independent and constrained refinement |
| $(\Delta/\sigma)_{max}$ | 0.001 |
| $\Delta\rangle_{max}$, $\Delta\rangle_{min}$ (e Å$^{-3}$) | 1.15, -0.88 |

Data collection: Bruker APEX3; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

Figure 13:
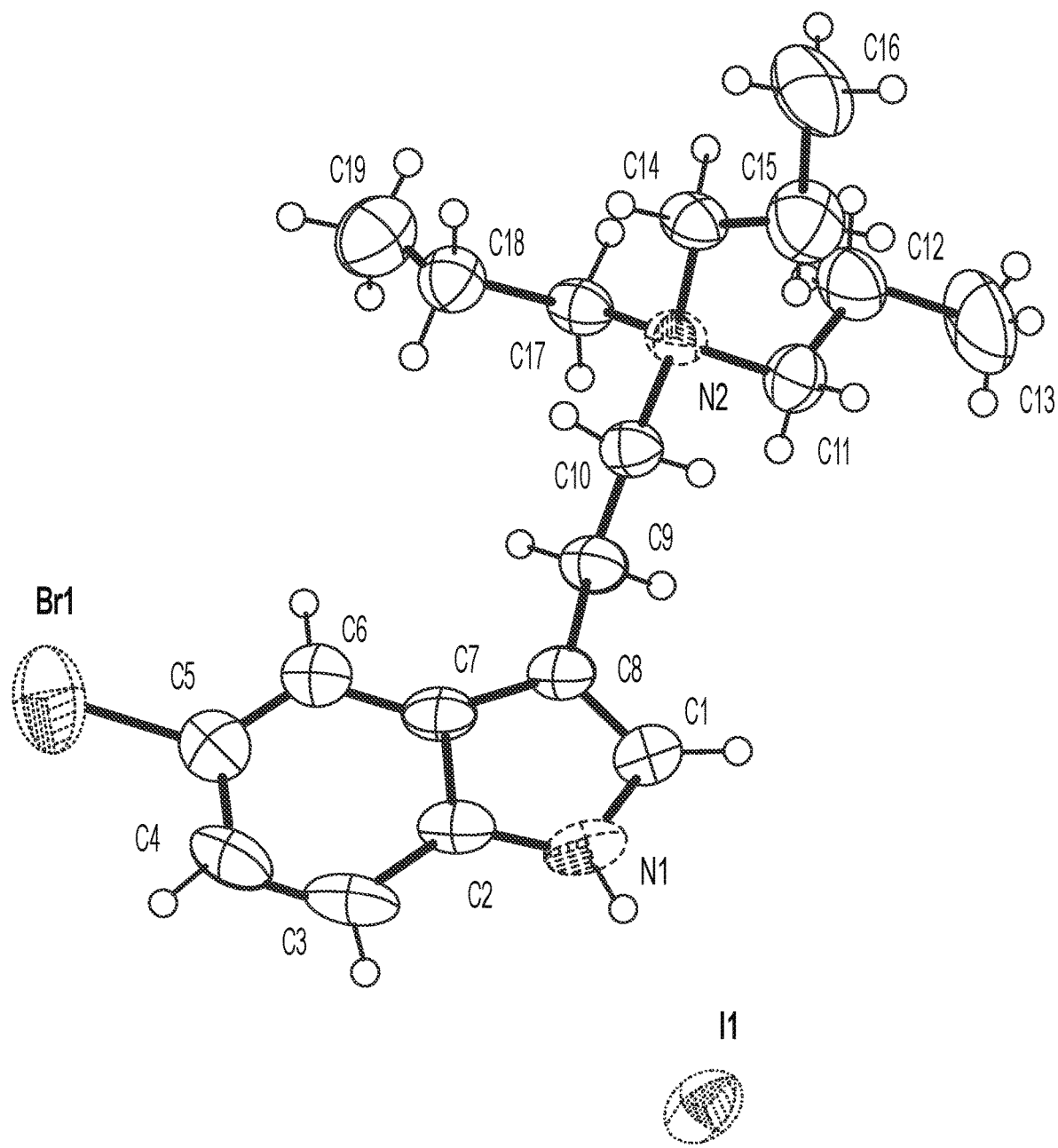
FIG. 13 shows the molecular structure of crystalline 5-bromo-N,N,N-tri-n-propyltryptammonium (5-Br-TPT) iodide, showing the atom labeling.

The molecular structure of crystalline 5-Br-TPT iodide, showing the atom labeling, is shown in FIG. 13.

Figure 14:
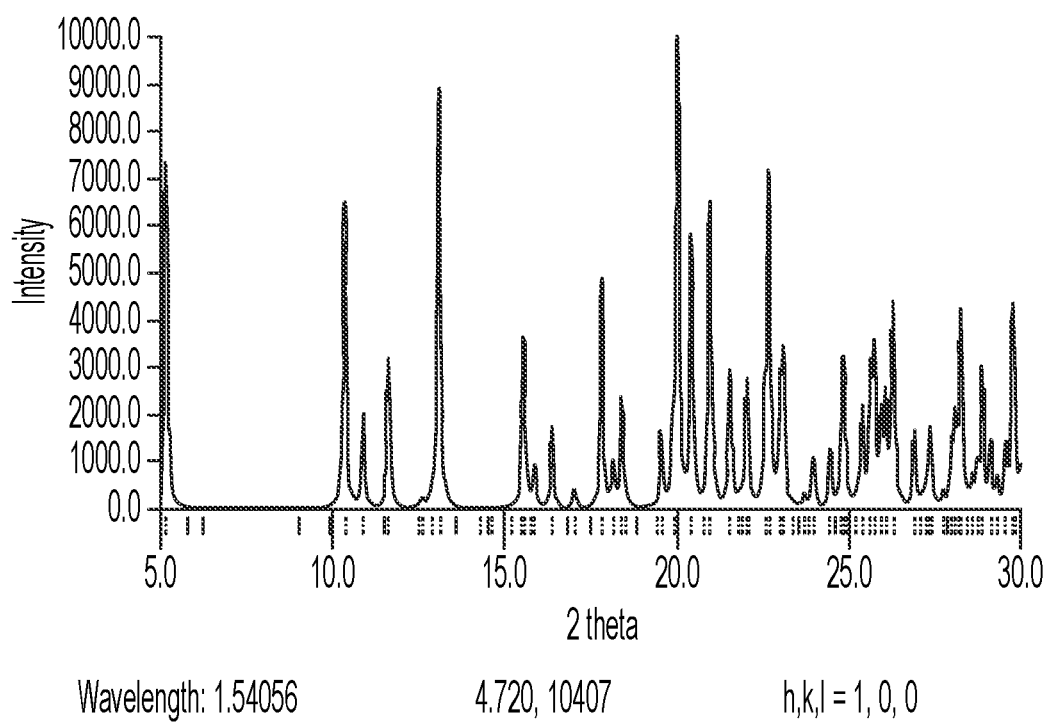
FIG. 14 shows a simulated x-ray powder diffraction (XRPD) of crystalline 5-Br-TPT iodide from its single crystal data.

FIG. 14 is a simulated x-ray powder diffraction (XRPD) of crystalline 5-Br-TPT iodide from its single crystal data. Crystalline 5-Br-TPT iodide may be characterized by the XRPD peaks at 5.2, 10.4, and 13.1° 2θ±0.2°2θ as well as by an XRPD pattern substantially similar to FIG. 14.

Example 8: Synthesis and Crystallization of 5-bromo-N,N,N-tri-n-propyltryptammonium (5-Br-TPT) iodide acetonitrile solvate 5-Br-TPT iodide acetonitrile solvate was synthesized via the same procedure used in Example 7, except crystals suitable for X-ray diffraction studies were grown from the slow evaporation of an acetone/acetonitrile solution.

Single crystal data, data collection and structure refinement details of crystalline 5-Br-TPT iodide acetonitrile solvate are summarized in Table 15.

TABLE 15

| | 5-bromo-N,N,N-tri-n-propyltryptammonium iodide acetonitrile solvate |
|---|---|
| Chemical formula | I•C$_{19}$H$_{30}$BrN$_2$•C$_2$H$_3$N |
| $M_r$ | 534.31 |
| Crystal system, space group | Monoclinic, P2$_1$/c |
| Temperature (K) | 297 |
| a, b, c (Å) | 11.4346 (5), 14.8646 (5), 14.9080 (6) |
| $\beta$ (°) | 107.269 (1) |
| V (Å$^3$) | 2419.70 (17) |
| Z | 4 |
| F(000) | 1072 |
| $D_x$ (Mg m$^{-3}$) | 1.467 |
| Radiation type | $M_o K_\alpha$ |
| $\lambda$ (Å) | 0.71073 |
| $\theta$ (°) | 2.9-26.1 |
| $\mu$ (mm$^{-1}$) | 2.98 |
| Crystal size (mm) | 0.34 × 0.25 × 0.2 |
| BLOCK | Colourless |
| Diffractometer | Bruker APEX-II CCD |
| Absorption correction | Multi-scan |
| | SADABS2016/2 (Bruker, 2016/2) was used for absorption correction. wR2(int) was 0.0565 before and 0.0454 after correction. The Ratio of minimum to |

TABLE 15-continued

| | 5-bromo-N,N,N-tri-n-propyltryptammonium iodide acetonitrile solvate |
|---|---|
| | maximum transmission is 0.8766. The $\lambda/2$ correction factor is not present. |
| $T_{min}$, $T_{max}$ | 0.567, 0.647 |
| No. of measured, independent, and observed [I > 2s(I)] reflections | 59383, 4956, 3949 |
| $R_{int}$ | 0.036 |
| $\theta_{max}$, $\theta_{min}$ (°) | 26.4, 2.9 |
| h, k, l | $-14 \to 14$, $-18 \to 18$, $-18 \to 18$ |
| Refinement | $F^2$ |
| $R[F^2 > 2\sigma(F^2)]$, $wR(F^2)$, S | 0.029, 0.069, 1.05 |
| w | $1/[\sigma^2(F_o^2) + (0.0217P)^2 + 2.4499P]$ where $P = (F_o^2 + 2F_c^2)/3$ |
| No. of reflections | 4956 |
| No. of parameters | 243 |
| No. of restraints | 0 |
| H-site location | mixed |
| H-atom treatment | H atoms treated by a mixture of independent and constrained refinement |
| $(\Delta/\sigma)_{max}$ | 0.002 |
| $\Delta\textgreater_{max}$, $\Delta\textgreater_{min}$ (e Å$^{-3}$) | 0.80, $-0.83$ |

Data collection: Bruker APEX3; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

Figure 15:
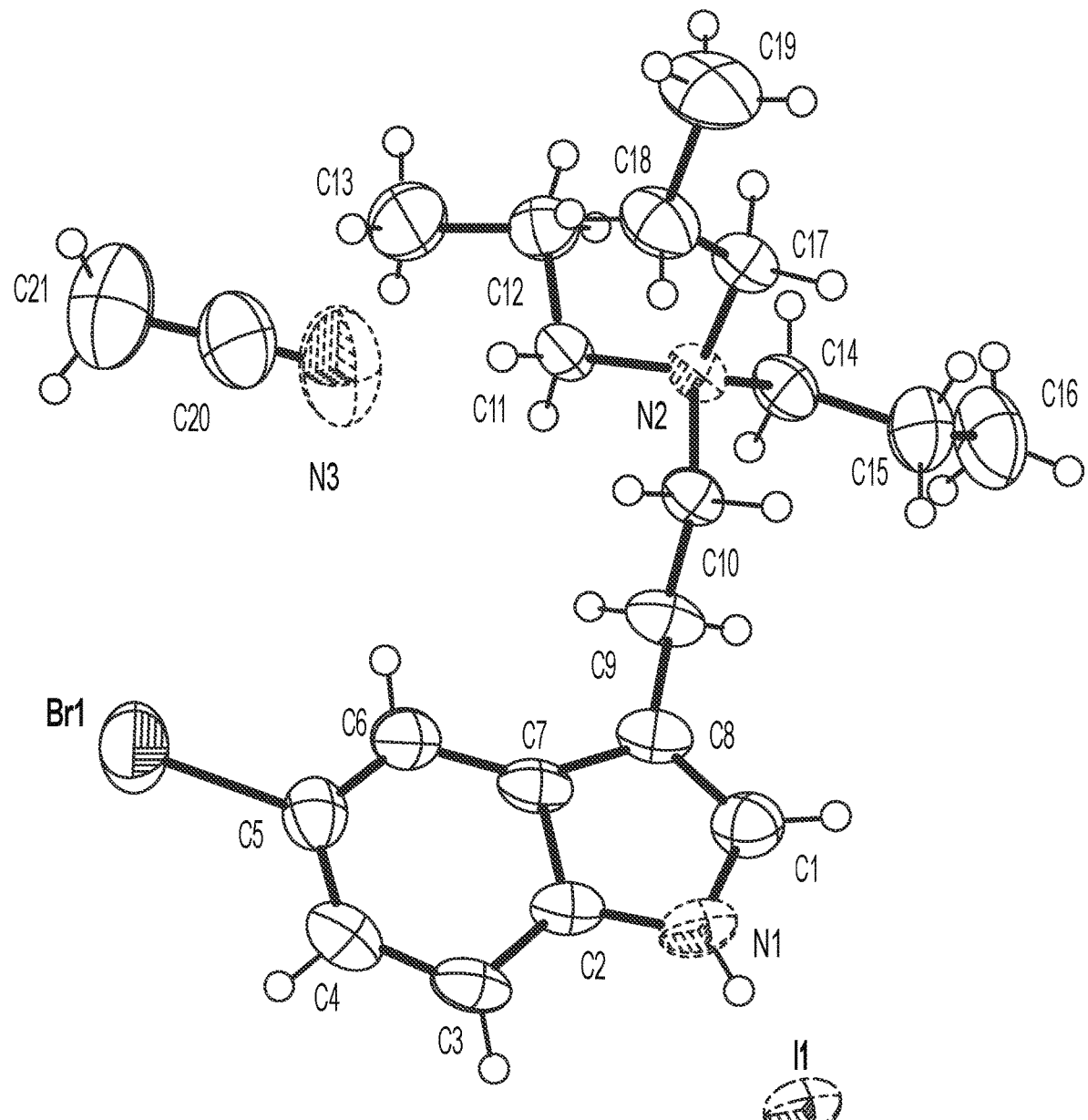
FIG. 15 shows the molecular structure of crystalline 5-bromo-N,N,N-tri-n-propyltryptammonium (5-Br-TPT) iodide acetonitrile solvate, showing the atom labeling.

The molecular structure of crystalline 5-Br-TPT iodide acetonitrile solvate, showing the atom labeling, is shown in FIG. 15.

Figure 16:
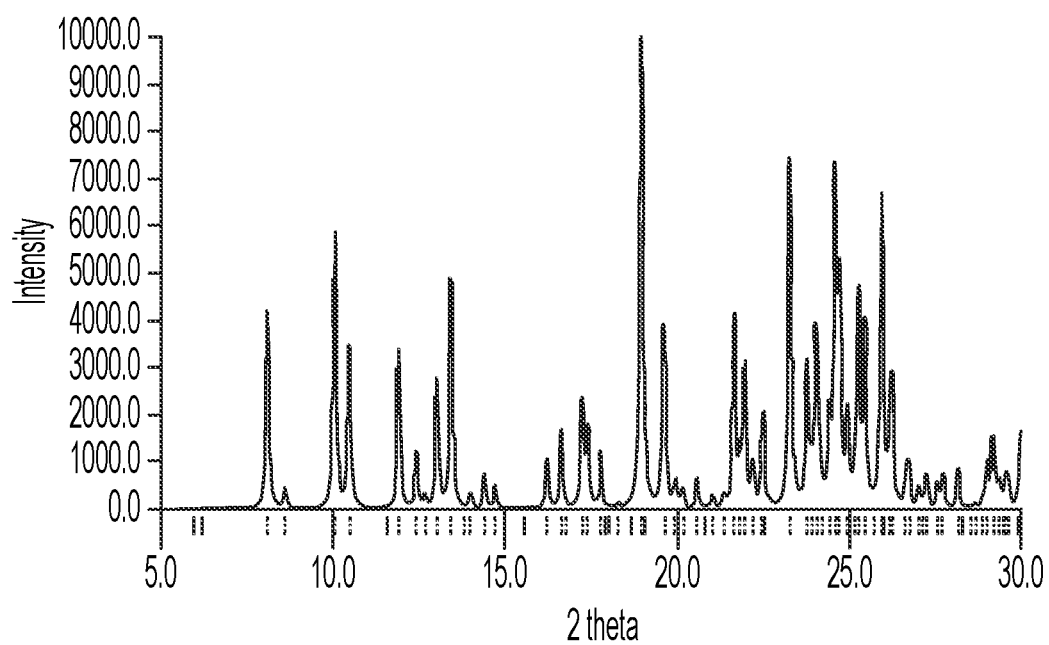
FIG. 16 shows a simulated x-ray powder diffraction (XRPD) of crystalline 5-Br-TPT iodide acetonitrile solvate from its single crystal data.

FIG. 16 is a simulated x-ray powder diffraction (XRPD) of crystalline 5-Br-TPT iodide acetonitrile solvate from its single crystal data. Crystalline 5-Br-TPT iodide acetonitrile solvate may be characterized by the XRPD peaks at 8.1, 10.0, and 11.9° 2θ±0.2° 2θ as well as by an XRPD pattern substantially similar to FIG. 16.

Example 9: Synthesis and Crystallization of 5-bromo-N,N,N-trimethyltryptammonium (5-Br-TMT) iodide 5-Br-TMT iodide was synthesized via the same procedure used in Example 7, except this procedure was repeated using a 5-bromo tryptamine in the presence of excess methyl iodide. Crystals suitable for X-ray diffraction studies were grown from the slow evaporation of an acetone/acetonitrile solution.

REFERENCES

Bradley, R. J. & Johnston, V. S. (1970). *Origin and Mechanism of Hallucinations*, edited by W. Keup, pp. 333-344. New York: Plenum Press.

Bruker (2018). *APEX3, SAINT, and SADABS*. Bruker AXS Inc., Madison, Wisconsin, USA.

Cameron, L. P. & Olson, D. E. (2018). *ACS Chem. Neurosci.* 9, 2344-2357.

Carhart-Harris, R. L. & Goodwin, G. M. (2017). *Neuropsychopharmacology*, 42, 2105-2113.

Chadeayne, A. R., Pham, D. N. K., Reid, B. G., Golen, J. A. & Manke, D. R. (2020). *ACS Omega*, https://doi.org/10.1021/acsomega.0c02208

Dinis-Oliveira, R. J. (2017). *Drug Metab. Rev.* 49, 84-91.

Dolomanov, O. V., Bourhis, L. J., Gildea, R. J., Howard, J. A. K. & Puschmann, H. (2009). *J. Appl. Cryst.* 42, 339-341. Farah, T. (2018). *Discover*, https://discovermagazine.com/health/beyond-psilocybin-mushrooms-have-lots-of-cool-compounds-scientists-should-study (accessed July, 2020)

J. Gartz, Int. *J. Crude Drug Res.*, 1989, 27, 141-144.

N. Jensen, J. Gartz and H. Laatsch, *Planta Med.*, 2006, 72, 665-666.

Johnson, M. W. & Griffithe, R. R. (2017). *Neurotherapeutics* 14, 734-740.

Lee, H. M., VanArenkonk, A. M. & Chen, K. K. (1936). *J. Pharmacol. Exp. Ther.* 56, 446-472.

McKenna, D. J., Repke, D. B., Lo, L. & Peroutka, S. J. (1990). *Neuropharmacology*, 29, 193-198.

Milne, N., Thomsen, P., Molgaard Knudsen, N., Rubaszka, P., Kristensen, M. & Borodina, I. (2020). *Metabolic Engineering*, 60, 25-36.

Nichols, D. E. (2012). *WIREs Membr. Transp. Signal.* 1, 559-579.

Repke, D. B., Grotjahn, D. B. & Shulgin, A. T. (1985). *J. Med. Chem.* 28, 892-896.

Revell, J. (2020). Vice, https://vice.com/en_in/article-y3zp35/magic-mushroom-paralysis-heres-what-we-know (accessed July, 2020)

Sheldrick, G. M. (2015a). *Acta Cryst.* A 71, 3-8

Sheldrick, G. M. (2015b). *Acta Cryst.* C71, 3-8.

Sherwood, A. M., Halberstadt, A. L., Klein, A. K., McCorvy, J. D., Kaylo, K. W., Kargbo, R. B. & Meisenheimer, P. J. (2020). *J. Nat. Prod.* 83, 461-467. Wieland, H., Konz, W. & Mittasch, H. (1934). *Justus Liebigs Ann. Chem.* 513, 1-25.

What is claimed is:

1. A quaternary amine compound of formula (I):

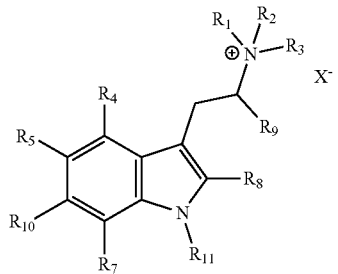

wherein:
- $R_1$, $R_2$, and $R_3$ are each independently chosen from a $C_1$-$C_6$ alkyl or $C_2$-$C_6$ alkenyl;
- one of $R_4$ and $R_5$ is hydrogen and the other of $R_4$ and $R_5$ is —$OSO_2R_6$;
- $R_6$ is a $C_1$-$C_6$ alkyl or a substituted or unsubstituted aryl;
- $R_7$, $R_8$, and $R_9$ are each independently hydrogen or $C_1$-$C_6$ alky;
- $R_{10}$ is selected from hydrogen, $C_1$-$C_6$ alkyl, $C_2$-$C_6$ alkenyl, halogen, hydroxy, —$OR_6$, —$OC(O)R_6$, —$OC(O)OR_6$, or —$OSO_2R_6$;
- $R_{11}$ is selected from hydrogen, $C_1$-$C_6$ alkyl, $C_2$-$C_6$ alkenyl, —$C(O)R_6$, —$C(O)OR_6$, or —$SO_2R_6$; and
- $X^-$ is a pharmaceutically acceptable anion.

2. A compound of formula (I) according to claim 1, wherein $R_4$ is hydrogen and $R_5$ is —$OSO_2R_6$.

3. A compound of formula (I) according to claim 1, wherein $R_5$ is hydrogen and $R_4$ is —$OSO_2R_6$.

4. A composition comprising a compound according to claim 1 and an excipient.

5. A pharmaceutical composition comprising a therapeutically effective amount of a compound according to claim 1 and a pharmaceutically acceptable excipient.

6. A composition comprising as a first active component: a compound according to claim 1; and as a second active component selected from (a) a serotonergic drug, (b) a purified psilocybin derivative, (c) one or two purified cannabinoids and (d) a purified terpene; and a pharmaceutically acceptable excipient.

7. A composition comprising as a first active component: a compound according to claim 1; and a second active component comprising an adrenergic drug or a dopaminergic drug; and a pharmaceutically acceptable excipient.

8. A composition comprising as a first active component: a compound according to claim 1; and a second active component comprising a purified monoamine oxidase inhibitor; and a pharmaceutically acceptable excipient.

9. A composition comprising as a first active component: a compound according to claim 1; and a second active component comprising a purified erinacine or a purified hericenone; and a pharmaceutically acceptable excipient.

10. A composition comprising a compound according to claim 2 and an excipient.

11. A composition comprising a compound according to claim 3 and an excipient.

12. A pharmaceutical composition comprising a therapeutically effective amount of a compound according to claim 2 and a pharmaceutically acceptable excipient.

13. A pharmaceutical composition comprising a therapeutically effective amount of a compound according to claim 3 and a pharmaceutically acceptable excipient.

14. A composition comprising as a first active component: a compound according to claim 2; and as a second active component selected from (a) a serotonergic drug, (b) a purified psilocybin derivative, (c) one or two purified cannabinoids and (d) a purified terpene; and a pharmaceutically acceptable excipient.

15. A composition comprising as a first active component: a compound according to claim 3; and as a second active component selected from (a) a serotonergic drug, (b) a purified psilocybin derivative, (c) one or two purified cannabinoids and (d) a purified terpene; and a pharmaceutically acceptable excipient.

* * * * *